United States Patent [19]
Janoff et al.

[11] Patent Number: 5,766,624
[45] Date of Patent: Jun. 16, 1998

[54] LIPOSOMAL DEFENSINS

[75] Inventors: Andrew S. Janoff, Yardley, Pa.; Walter Perkins, Monmouth Junction; Imran Ahmad, Plainsboro, both of N.J.

[73] Assignee: The Liposme Company, Inc., Princeton, N.J.

[21] Appl. No.: 449,598

[22] Filed: May 24, 1995

Related U.S. Application Data

[63] Continuation of Ser. No. 142,691, Oct. 25, 1993, abandoned.

[51] Int. Cl.$^6$ .................................................. A61K 9/127
[52] U.S. Cl. .................................................. 424/450; 424/417
[58] Field of Search .................................................. 424/450, 417; 514/2, 21

[56] References Cited

U.S. PATENT DOCUMENTS

| | | | |
|---|---|---|---|
| 4,229,360 | 10/1980 | Schneider et al. | 260/403 |
| 4,522,803 | 6/1985 | Lenk et al. | 424/1.1 |
| 4,588,578 | 5/1986 | Fountain et al. | 424/1.1 |
| 4,837,028 | 6/1989 | Allen et al. | 424/450 |
| 4,880,635 | 11/1989 | Janoff et al. | 424/450 |
| 4,920,016 | 4/1990 | Allen et al. | 424/450 |
| 4,962,277 | 10/1990 | Cuervo et al. | 514/14 |
| 4,975,282 | 12/1990 | Cullis et al. | 424/450 |
| 5,008,050 | 4/1991 | Cullis et al. | 264/4.3 |
| 5,013,556 | 5/1991 | Woodle | 424/450 |
| 5,030,453 | 7/1991 | Lenk et al. | 424/450 |
| 5,032,574 | 7/1991 | Wilde et al. | 514/12 |
| 5,045,531 | 9/1991 | Berkowitz et al. | 514/12 |
| 5,059,421 | 10/1991 | Loughrey et al. | 424/417 |
| 5,077,056 | 12/1991 | Bally et al. | 424/450 |
| 5,169,637 | 12/1992 | Lenk et al. | 424/450 |
| 5,204,112 | 4/1993 | Hope et al. | 124/450 |
| 5,252,263 | 10/1993 | Hope et al. | 264/4.3 |
| 5,279,833 | 1/1994 | Rose | 424/450 |

FOREIGN PATENT DOCUMENTS

| | | | |
|---|---|---|---|
| 89/03677 | 5/1989 | WIPO | A61K 9/50 |
| 89/11291 | 11/1989 | WIPO | A61K 37/02 |
| 91/04019 | 4/1991 | WIPO | A61K 9/50 |

OTHER PUBLICATIONS

Cociancich et al JBC, 268 #26, p. 19239, Sep. 93.
Cullis in Liposomes from Biophysics to Therapeutics Ostro Ed. Chapter II, Marcel Dekker NY 1987.
Fujii et al. Protein Science 2, p. 1301, 1993.
Georghious, et al., "Melittin–Phospholipid interaction studied by employing the single tryptophan residue as an intrinsic fluorescent probe", Chemical Abs, 97:51414y, 97, 244, (1982).
Vaz Gomes, et al., "Electric Potentiation, Cooperativity, and Synergism of Magainin Peptides in Protein–Free Liposomes", Biochemistry, 32, 5365–5372, 1993.
Williams, et al., "Raman Spectroscopy of Synthetic Antimicrobial Frog Peptides Magainin 2a and PGLa", Biochemistry, 29, 4490–4496, 1990.
Bangham, et al., "Diffusion of Univalent Ions across the Lamellae of Swollen Phosphlipids", J. Mol. Bio. 13:238–252, 1965.

(List continued on next page.)

*Primary Examiner*—Gollamudi S. Kishore
*Attorney, Agent, or Firm*—Kenneth B. Rubin

[57] ABSTRACT

Defensins are microbicidal, tumoricidal cytotoxic protein components of animal host defense systems. They can be entrapped in liposomes containing release-inhibiting lipid such that the defensins are neutralized, and their release from the liposomes is inhibited; however, the defensins remain effective when exposed to endocytosed material in endocytic vesicles. Liposomal defensin formulations are administered to animals for the treatment or prevention of microbial infections, for the treatment of cancers and for the treatment of disorders characterized by a deficiency of protein-mediated cytotoxic activity in cytoplasmic granules.

22 Claims, 14 Drawing Sheets

OTHER PUBLICATIONS

Blume, et al., "Specific targeting with poly(ethylene glycol)–modified liposomes: coupling of homing devices to the ends of the polymeric chains combines effective target binding with long circulation times", Biochem. Biophys. Acta. 1149:180–184, 1993.

Charp et al. "Inhibition of Protein Kinase C by Defensins, Antibiotic Peptides from Human Neutrophils", Biochem. Pharmacol. 37(5).:951, 1988.

Chen et al., "Microdetermination of Phosphorus", Anal. Chem. 28:1956, 1956.

Cullis, et al., in:*Liposomes, From Biophysic to Therapeutics*, M. J. Ostro, Ed., Marcel Dekker, pp. 39–72, 1987.

Daher, et al., "Direct Inactivation of Viruses by Human Granulocyte Defensins", J. Virol. 60(3), 1068, 1986.

Gabay, et al., "Subcellular Location and Properties of Bactericidal Factors From Human Neutrophils", J. Exp. Med. 164:1407, 1986.

Gabison, et al., "Prolongation of the Circulation Time of Doxorubicin Encapsulated in Liposomes Containing a Polyethylene Glycol–Derivativzed Phospholipid: Pharmacodinetic Studies in Rodents and Dogs", Pharm. Res. 10(5):703, 1993.

Ganz, et al., "Defensins: microbicidal and cytotoxic peptides of mammalian host defense cells", Med. Microbiol. Immunol. 181:99 (1992).

Ganz, "Defensins", Eur. J. Haematol, 44:1, 1990.

Gruner, S. Nonlamellar Lipid Phases, in: *The Structure of Biological Membranes* (P. Yeagle, ed.), CRC Press, Inc., Boca Raton (1992), pp. 222–223.

Hoffman, et al. "Insect defensins: inducible antibacterial peptides", Immunology Today, 13(10):411, 1992.

Kagan, et al., "Antimicrobial defensin peptides from voltage–dependent ion–permeable channels in planar lipid bilayer membranes", PNAS 87:210, 1990.

Lichtenstein, et al., "Mechanism of Target Cytolysis by Peptide Defensins", J. Immunol. 140:2686, 1988.

Lichtenstein, et al., "In Vitro Tumor Cell Cytolysis Mediated by Peptide Defensins of Human and Rabbit Granulocytes", Blood 68(6):1407, 1986.

Papahadjopoulos et al., "Phospholipid Model Membranes, I. Structural Characteristics of Hydrated Liquid Crystals", Biochem. Biophys. Acta. 135:624 (1968).

Park et al., "Some negatively charged phospholipid derivatives prolong the liposome circulation in vivo", Biochim. Biophys. Acta, 1108:257–260, 1992.

Rice, et al., "Defensin–Rich Dense Granules of Human Neutrophils", Blood, 70(3):757, 1987.

Selsted, et al., "Indolicidin, A Novel Bactericidal Tridecapeptide Amide from Neutrophils", J. Biol. Chem.267(7):4292–4295, 1992.

Selsted, et al., "Purification, Primary Structures, and Antibacterial Activities of β–Defensins, a New Family of Antimicrobial Peptides from Bovine Neutrophils", J. Biol. Chem, 268(9):6641, 1993.

Fluorescence of Free and Liposomal Indolicidin

Effect of Different Lipids on Red Blood Cell Hemolysis

Effect of DOPE On the Hemolysis of Red Blood Cells

Therapeutic Efficacy of Free and Liposomal Indolicidin Against Systemic Aspergillosis in Balb/C Mice

LIPOSOMAL DEFENSINS

This application is a FWC of U.S. Ser. No. 08/142,691, filed Oct. 25, 1993 which is abandoned.

This work was conducted in part under Grant No. AI31696-01 from the National Institutes of Health. Accordingly, the United States government has certain rights to the invention.

This application is directed to liposomal defensin formulations and their therapeutic use. Defensins are protein components of an animal's host defense system. They are found in the specialized cells responsible for destroying invading microbes and parasites, as well as abnormal or senescent cells, in an animal. Both Gram-positive and Gram-negative bacteria, fungi, and parasites are subject to defensin action (see, e.g., T. Ganz et al., Med. Microbiol. Immunol. 181:99 (1992)). Defensins also inactivate viruses. In this regard, Daher et al. reported (J. Virol. 60(3):1068 (1986)) that human defensins inactivated enveloped viruses such as herpes simplex virus types 1 and 2, cytomegalovirus, vesicular stomatitis virus and an influenza virus. Ganz et al. report (Eur. J. Haematol. 44:1 (1990)) that several defensins killed mammalian cells in culture. Lichtenstein et al. (Blood 68(6):1407 (1986)) reported that human defensins were capable of lysing murine and human lymphoma cells. Rabbit defensins were also cytotoxic to murine lymphomas. Furthermore, Charp et al. (Biochem. Pharmacol. 37(5):951 (1988)) reported that the human defensins (HNP-1, HNP-2 and HNP-3) inhibited protein kinase C activity.

Defensins are found in such mammals as humans, cows, rabbits, guinea pigs and rats. The typical mammalian defensins are cationic, amphiphilic proteins of about 29–34 amino acids, having a conserved pattern of six cysteine residues. However, not all defensins found in mammalian cytoplasmic granules fit this prototypical pattern. Indolicidin, for example, is a cytotoxic, tryptophan-rich, thirteen amino-acid defensin derived from bovine neutrophils (see M. Selsted et al., J. Biol. Chem 267(7):4292 (1992)). The same group (see Selsted et al., J. Biol. Chem. 268(9):6641 (1993)) reported the isolation of beta-defensins, a family of cationic, amphiphilic proteins with six conserved cysteine residues having cytotoxic activities similar to those of the prototypical mammalian defensins, although their sizes and structures are somewhat different. Magainins, proteins originally obtained from frogs, are also similar to the mammalian defensins (see, e.g., U.S. Pat. No. 4,962,277; U.S. Pat. No. 5,045,531). Defensins have also been found in insects (for a review, see J. Hoffman and C. Hetru, Immunology Today 13(10):411 (1992).

Phagocytes such as neutrophils, eosinophils, macrophages and killer lymphocytes have defensin-containing cytoplasmic granules, with neutrophils being a particularly rich source of defensins. The cytoplasmic granules fuse with endocytic vesicles, allowing the defensins to come into contact with endocytosed material such as invading microbes (see J. Gabay et al., J. Exp. Med. 164:1407 (1986); W. Rice et al., Blood 70(3):757 (1987)).

Defensins can bind to and permeabilize the external phospholipid membranes of their targets, thereby disrupting the cell's osmotic balance (see, e.g., Ganz et al., Med. Microbiol. Immunol. 181:99 (1992); Ganz et al., Eur. J. Haematol. 44:1 (1990); Kagan et al., PNAS 87:210 (1990); Lichtenstein et al., J. Immunol. 140:2686 (1988); Lichtenstein et al., Blood 68(6):1407 (1986)). This permeabilization may or may not be sufficient in and of itself to induce cell death; target cell metabolic activity and further defensin action can also be required.

Achieving the full therapeutic potential of defensins in animals requires that the proteins must be administered in such a way that they reach their targets in an active form but avoid collateral damage to the animal's normal cells. This may be accomplished by entrapping the defensins in liposomes.

Liposomes are self-assembling structures comprising one or more bilayers of amphipathic lipid molecules enclosing an internal aqueous volume. The amphipathic lipid molecules which make up lipid bilayers comprise a polar (hydrophilic) headgroup region covalently linked to one or two non-polar (hydrophobic) acyl chains. The energetically unfavorable contact between the hydrophobic acyl chains and the aqueous medium causes the lipid molecules to rearrange such that the polar headgroups are oriented towards the aqueous medium while the acyl chains reorient towards the interior of the bilayer. The net result is an energetically stable structure in which the acyl chains are effectively shielded from coming into contact with the aqueous medium.

Liposomes may be produced by a variety of methods (for a review, see, e.g., Cullis et al., in: *Liposomes, From Biophysics to Therapeutics* M. J. Ostro, ed.), Marcel Dekker, pp. 39–72 (1987)). Bangham's procedure (J. Mol. Biol. 13:238–252 (1965)) produces ordinary multilamellar vesicles (MLVs). Lenk et al. (U.S. Pat. Nos. 4,522,803 (PCT Publication No. WO 83/03383 (Oct. 13, 1983), 5,030,453 and 5,169,637), Fountain et al. (U.S. Pat. No. 4,588,578 (PCT Publication No. WO 85/00751 (Feb. 28, 1985)) and Cullis et al. (U.S. Pat. No. 4,975,282 (PCT Publication No. WO 87/00043 (Jan. 15, 1987)) disclose methods for producing multilamellar liposomes having substantially equal interlamellar solute distribution.

Unilamellar vesicles can be produced from MLVs by sonication (see Paphadjopoulos et al., Biochem. Biophys. Acta. 135:624 (1968)) or extrusion (Cullis et al., (U.S. Pat. No. 5,008,050 (PCT Publication No. WO 86/00238 (Jan. 16, 1986)) and Loughrey et al., U.S. Pat. No. 5,059,421 (PCT Publication No. WO 91/00289 (Jan. 10, 1989)). Janoff et al. (U.S. Pat. No. 4,721,612 (PCT Publication No. 85/04578 (Oct. 24, 1985)) and Bolcsak et al. (U.S. Pat. No. 5,100,662) describe the use of sterols for the preparation of liposomes having enhanced stability. These disclosures are incorporated herein by reference to indicate the state of the art with respect to liposome preparation.

Liposomes can be loaded with bioactive agents passively, i.e., by solubilizing the molecule in the medium in which the liposomes are formed, in the case of water-soluble agents, or adding lipid-soluble agents to the lipid solutions from which the liposomes are made. Ionizable bioactive agents can also be loaded into liposomes actively, e.g., by establishing an electrochemical potential gradient across the liposomal membrane and then adding the agent to the medium external to the liposome (see Bally et al., U.S. Pat. No. 5,077,056, the contents of which are incorporated herein by reference).

Drugs entrapped within liposomes can have an enhanced therapeutic index by reducing toxicity, increasing efficacy, or both. Furthermore, liposomes, like other particulate matter in the circulation, are taken up by phagocytic cells of the reticuloendothelial system in tissues having sinusoidal capillaries, and are thereby often directed to the sites of intracellular infections.

Applicants provide herein a liposome containing a defensin and a release-inhibiting lipid, wherein the defensin is a neutralized defensin, i.e., a defensin whose release from the liposome is inhibited. U.S. Pat. No. 5,032,574 disclose liposomes containing an antimicrobial protein whose sequence, although altered, is based upon the conserved mammalian defensin sequence. However, this reference does not disclose liposomes designed to inhibit the release of defensins entrapped therein.

SUMMARY OF THE INVENTION

This application provides a liposome comprising a lipid bilayer, an aqueous compartment and a defensin, wherein the defensin is a neutralized defensin. The liposome may be unilamellar or multilamellar, but is preferably multilamellar. More preferably, the liposome is a multilamellar liposome having a solute entrapped in its aqueous compartments, wherein the concentration of the solute in each of the aqueous compartments is substantially equal, i.e., the liposome is a multilamellar vesicle having substantially equal interlamellar solute distribution. The defensin can be contained in a lipid bilayer of the liposome and/or in an aqueous compartment of the liposome. The defensin can be any microbicidal and/or tumoricidal animal host defense system protein, e.g., a prototypical mammalian defensin, beta-defensin, indolicidin, magainin or insect defensin. Presently, the preferred defensin is indolicidin.

The liposome of this invention can comprise a release-inhibiting lipid. Presently preferred release-inhibiting lipids are 1-palmitoyl-2-oleoyl phosphatidylcholine (POPC), dioleoyl phosphatidylcholine (DOPC) and distearoyl phosphatidylcholine (DSPC) plus cholesterol, preferably at a DSPC to cholesterol ratio (mole/mole) of about 3:2. Accordingly, in presently preferred embodiments of the invention, the defensin is indolicidin and the liposome comprises a release-inhibiting lipid comprising POPC, DOPC or DSPC and cholesterol. Indolicidin/POPC liposomes typically comprise at least about 0.5 mole percent indolicidin and at most about 99.5 mole percent POPC, preferably, about 5 mole percent indolicidin and about 95 mole percent POPC. Indolicidin/(DSPC plus cholesterol) liposomes typically comprise at least about 0.5 mole percent indolicidin and at most about 99.5 mole percent DSPC plus cholesterol, preferably, about 20 mole percent indolicidin and about 80 mole percent DSPC plus cholesterol. Indolicidin/DOPC liposomes typically comprise at least about 5 mole percent indolicidin and at most about 95 mole percent DOPC.

Liposomes provided herein may further comprise a release-inhibiting aqueous buffer, a headgroup-modified lipid and an additional bioactive agent. The liposomes may further comprise a lipid bilayer which comprises an ionizable lipid. Preferably, greater than about 50 percent of the ionizable lipid present in the outermost lipid bilayer of the liposome is present in the inner monolayer of the outermost lipid bilayer. Typically, the ionizable lipid comprises at least about five mole percent of the lipid in the lipid bilayer, desirably, about ten mole percent. In a presently preferred embodiment of the invention, the ionizable lipid comprises DPDAP (1,2-dipalmitoyl-3-(N,N-dimethylamino)-propane.

This invention also provides a dehydrated liposome comprising a defensin, wherein the defensin is a neutralized defensin. Further provided is a pharmaceutical composition comprising a pharmaceutically acceptable carrier and a liposome comprising a lipid bilayer, an aqueous compartment and a defensin, wherein the defensin is a neutralized defensin.

Anti-infection effective amounts of the pharmaceutical composition may be administered to animals for the treatment or prevention of infections by organisms sensitive to a defensin, e.g., indolicidin. Preferred therapeutic subjects are mammals, particularly, humans, for example those humans whose immune systems have been compromised, e.g., by viruses such as HIV, by chemotherapy or for organ transplantation. Infections caused by fungi sensitive to a defensin, such as those infections caused by Cryptococcus or Aspergillus fungi, can be treated with the liposomes of this invention. Accordingly, in a presently preferred embodiment of the invention, the animal treated is an immunocompromised human and the infection comprises a fungal infection by a Cryptococcus or an Aspergillus.

Anticancer effective amounts of the pharmaceutical composition provided herein can be administered to animals for the treatment of cancers responsive to a defensin, e.g., a leukemia or a lymphoma.

Further provided herein is a method of treating an animal for a disorder, e.g., Specific Granule Deficiency Syndrome, characterized by a deficiency of protein-mediated microbicidal and/or tumoricidal cytotoxic activity in cytoplasmic granules, which comprises administering to the animal a cytotoxic effective amount of the pharmaceutical composition provided herein. This method may be particularly useful for treating animals afflicted with such a syndrome which also have a microbial infection.

Indolicidin-containing liposomes were formed with distearoyl phosphatidylcholine (DSPC) plus cholesterol as described below. The concentration of indolicidin in the supernatant, and hence, the level of the indolicidin originally entrapped which subsequently leaks from the liposomes, was determined in accordance with the procedures described below. The concentration of indolicidin in the supernatant (mM) is given after the first, second, third, fourth, fifth and sixth washings.

Figure 6:
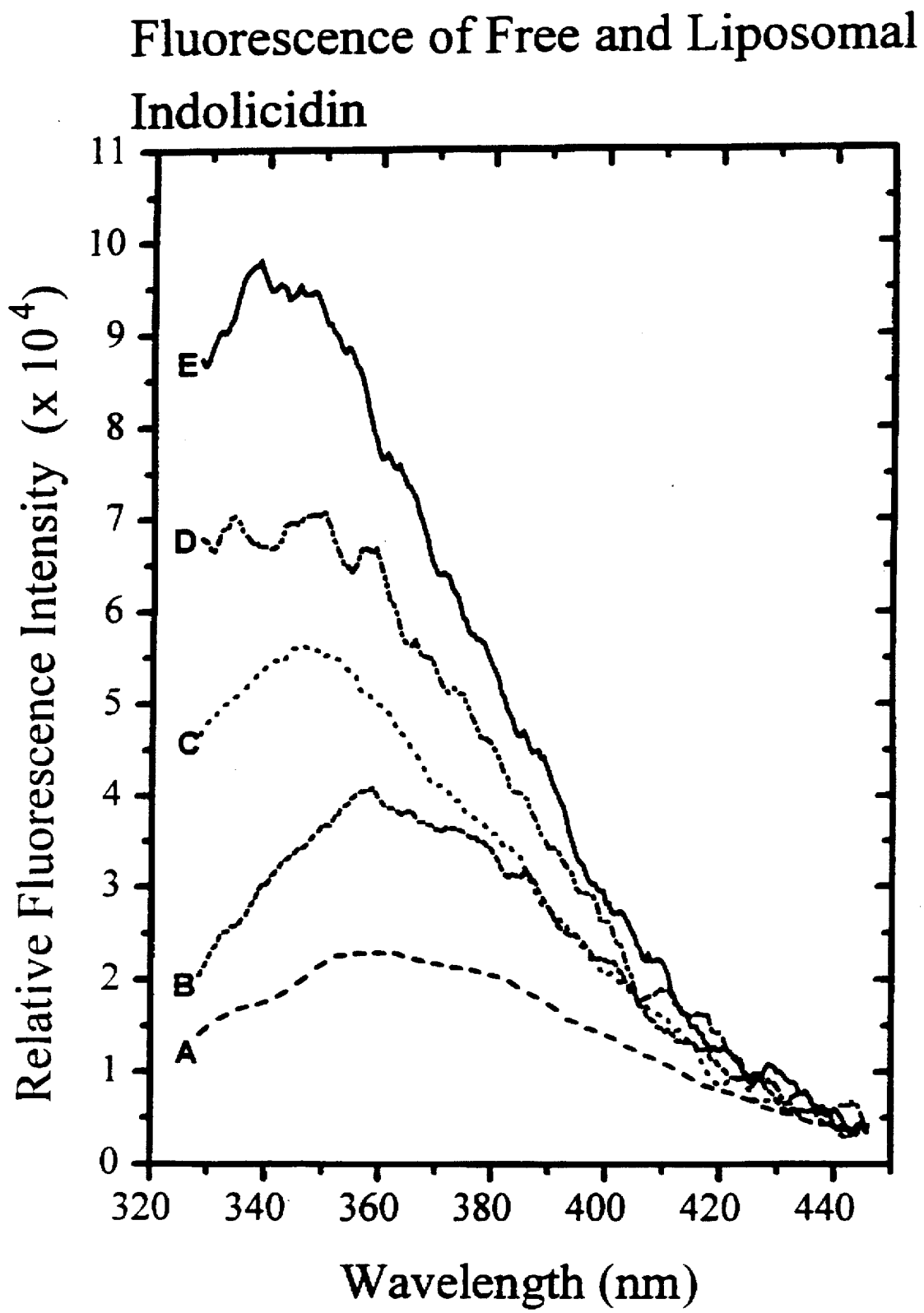

FIG. 6. Fluorescence of Fee and Liposomal Indolicidin. POPC, DOPC and DSPC/Chol (3:2) multilamellar vesicles (MLVs) were extruded through two stacked polycarbonate filters of 0.1 micron pore size at 50 degrees C. Aliquots of the resulting liposome samples were diluted to a final lipid concentration of 0.1 mg/ml and fluorescence emission profiles were taken with, and without, 0.5 µg indolicidin present. Emission wavelengths were scanned from 325 nm to 450 nm; the excitation wavelength was set at 285 nm. A: Indolicidin in buffer solution; B: indolicidin/DPPC/Chol liposomes; C: indolicidin/DOPC liposomes; D: indolicidin/POPC/Chol liposomes; E: indolicidin/POPC liposomes.

Figure 7:
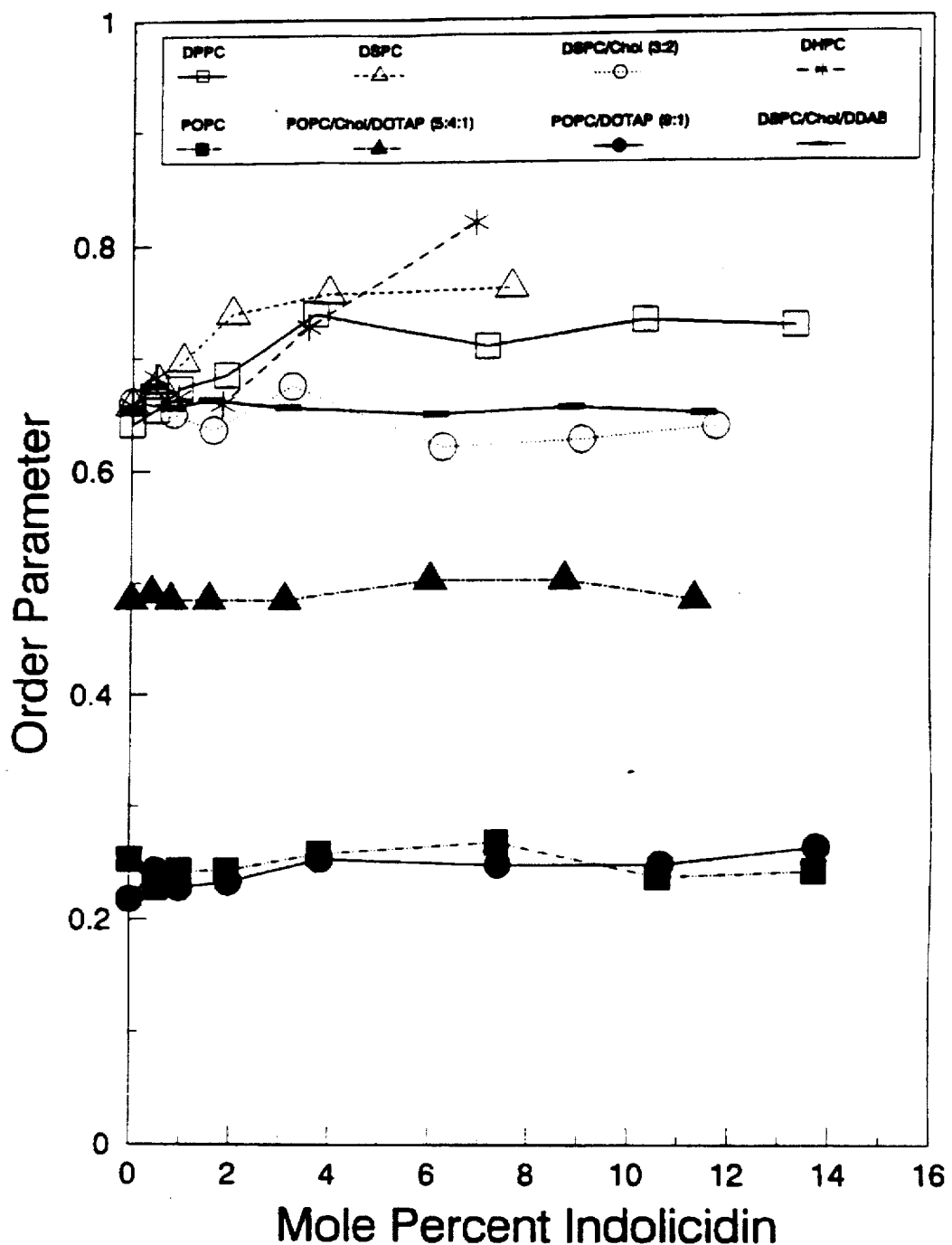

FIG. 7. Order Parameter of Liposomal Indolicidin Systems. The vertical axis shows the effect on the order parameter of various liposomal systems of the addition of indolicidin at increasing indolicidin concentrations (mole percent, horizontal axis) using the spin label 1-palmitoyl-2(12 doxyl stearoyl)-phosphatidylcholine at a concentration of 1 mole percent. Open squares: DPPC liposomes; open triangles: DSPC liposomes; open circles: DSPC/Chol (3:2) liposomes; asterisks: DHPC liposomes; filled squares: POPC liposomes; filled triangles: POPC/Chol/DOTAP (dioleoyl trimethylamino propane) (5:4:1) liposomes; filled circles: POPC/DOTAP (9:1) liposomes; and filled bars: DSPC/Chol/DDAB (dimethylamino dioctadecyl ammonium bromide) liposomes.

Figure 8:
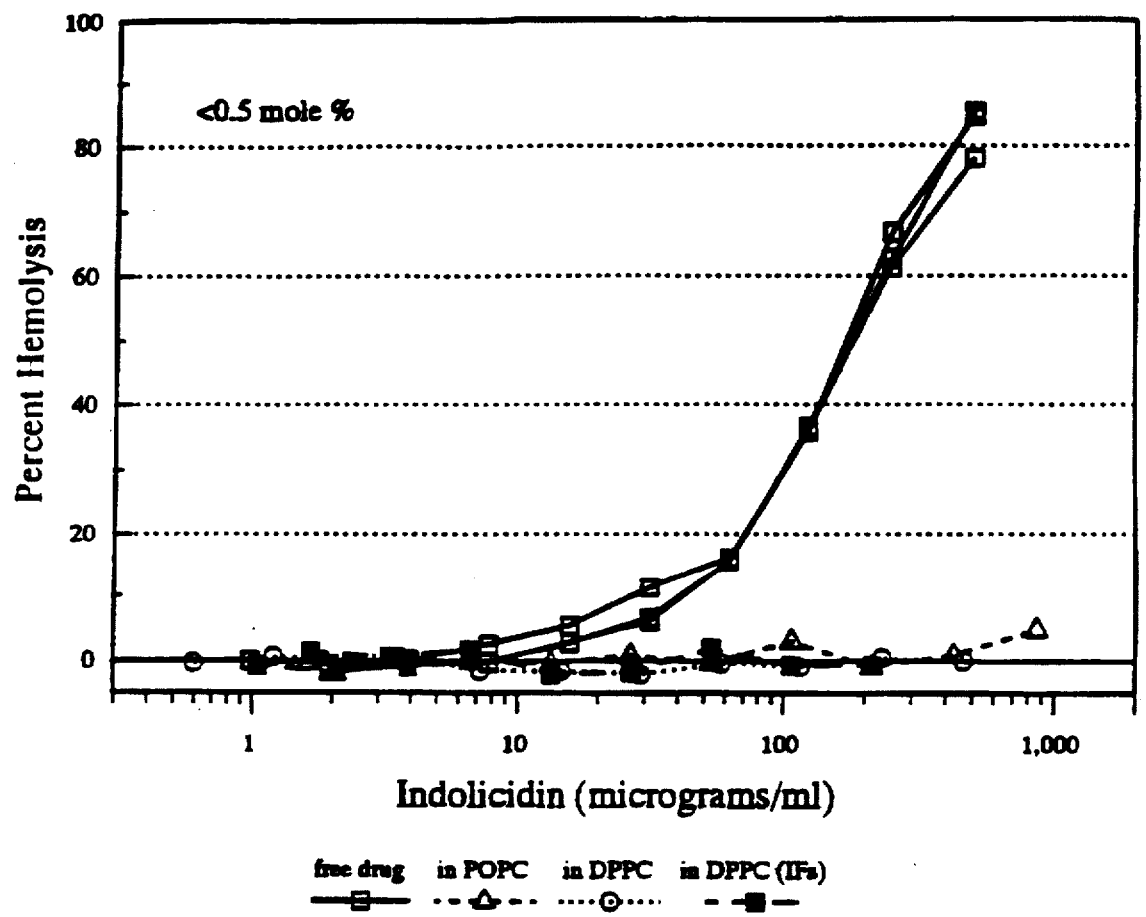

FIG. 8. Hemolytic Activity of Indolicidin in POPC- and DPPC-Containing Liposomes. Indolicidin, both in its free (unentrapped) form, and as part of liposomal formulations, was incubated with red blood cells (RBCs). The percentage of the RBCs lysed was measured as described below and is given as a function of indolicidin concentration (open squares: free indolicidin; open triangles: indolicidin/POPC liposomes; open circles: indolicidin/DPPC liposomes; filled squares: indolicidin/DPPC interdigitation-fusion liposomes).

Figure 9:
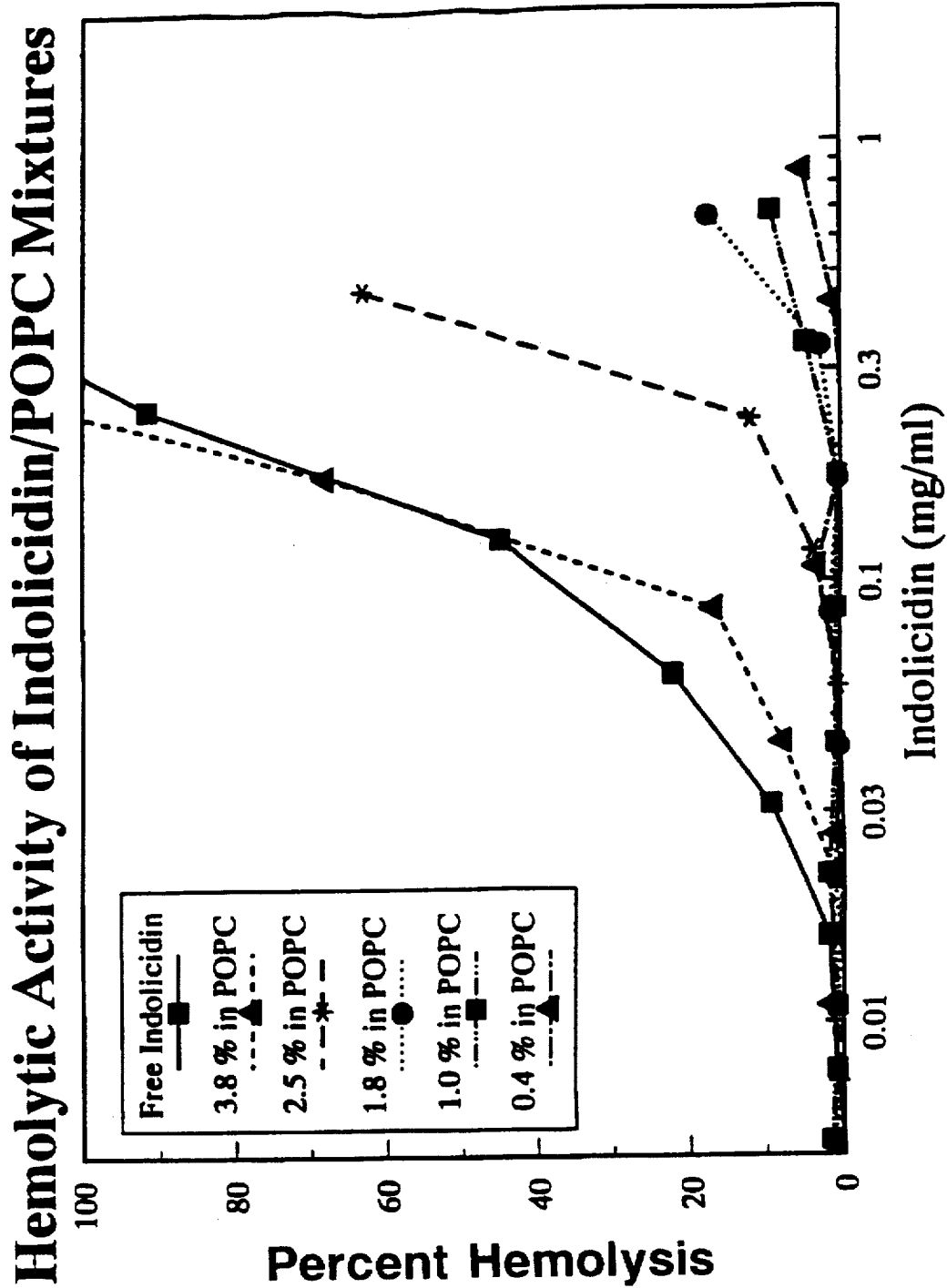

FIG. 9. Effect of Varying the Concentration of Indolicidin in POPC-Containing Liposomes on Hemolytic Activity. Indolicidin/POPC liposomes were prepared as described below. The indolicidin-containing vesicles (along with free indolicidin) were incubated with RBCs, and the number lysed was determined (also in accordance with procedures described below). The percentage of RBC hemolysis induced by indolicidin is given as a function of indolicidin concentration (mg/ml) in the RBC samples (filled squares: free indolicidin; filled triangles: 3.8 mole percent indolicidin in POPC liposomes; stars: 2.5 mole percent indolicidin; filled circles: 1.8 mole percent indolicidin; filled squares: 1.0 mole percent indolicidin; filled triangles: 0.4 mole percent indolicidin).

Figure 10:
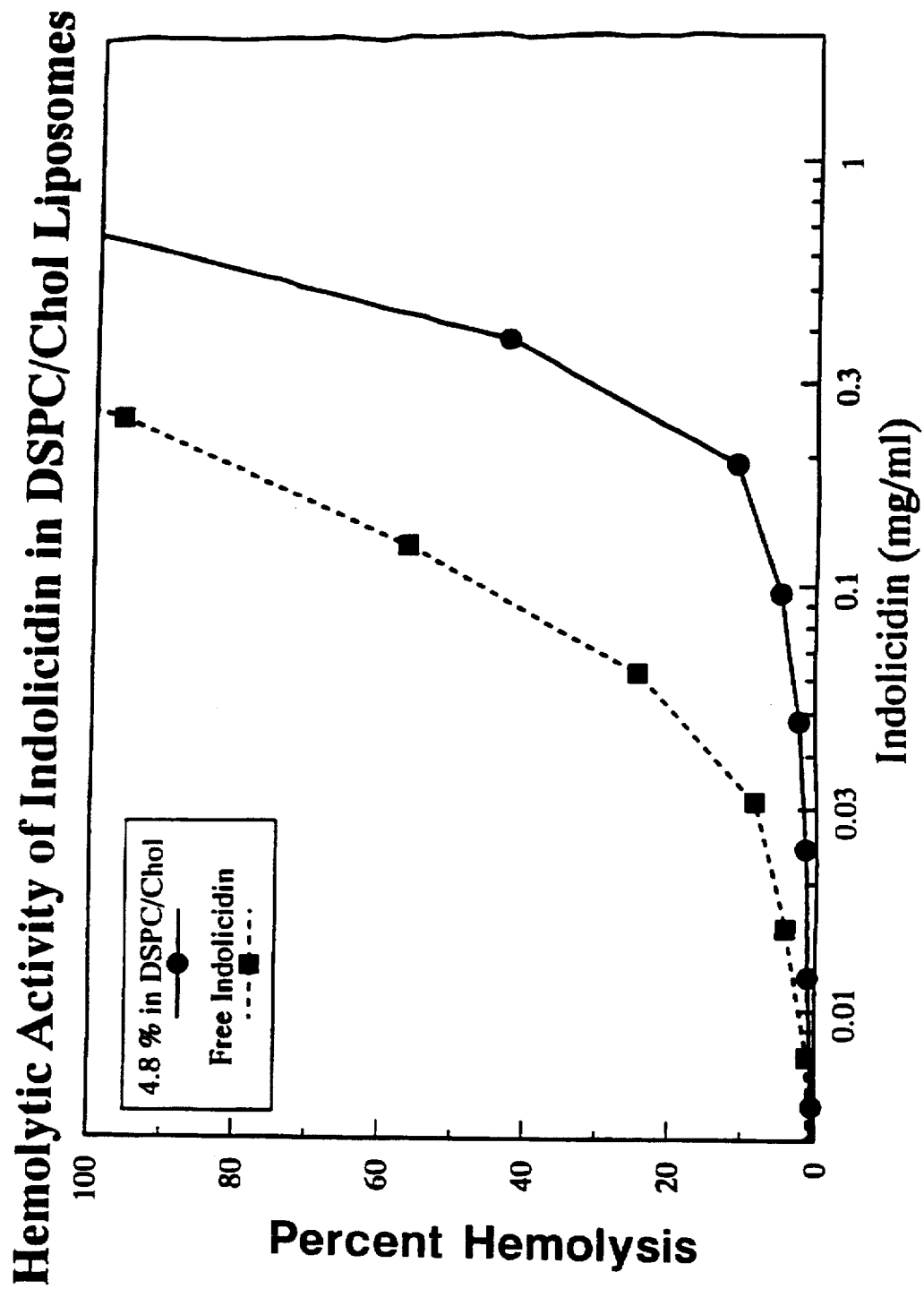

FIG. 10. Hemolytic Activity of Indolicidin in DSPC/Chol Liposomes. Indolicidin-containing DSPC/Chol liposomes were prepared, as described below, to have 4.8 mole percent indolicidin. The liposomes were incubated with RBCs. The number lysed, determined as described below, is given as the percent of RBC hemolysis observed with varying the indolicidin concentration in the RBC samples (filled circles: 4.8 mole percent indolicidin in DSPC/Chol liposomes; filled squares: free indolicidin).

Figure 11:
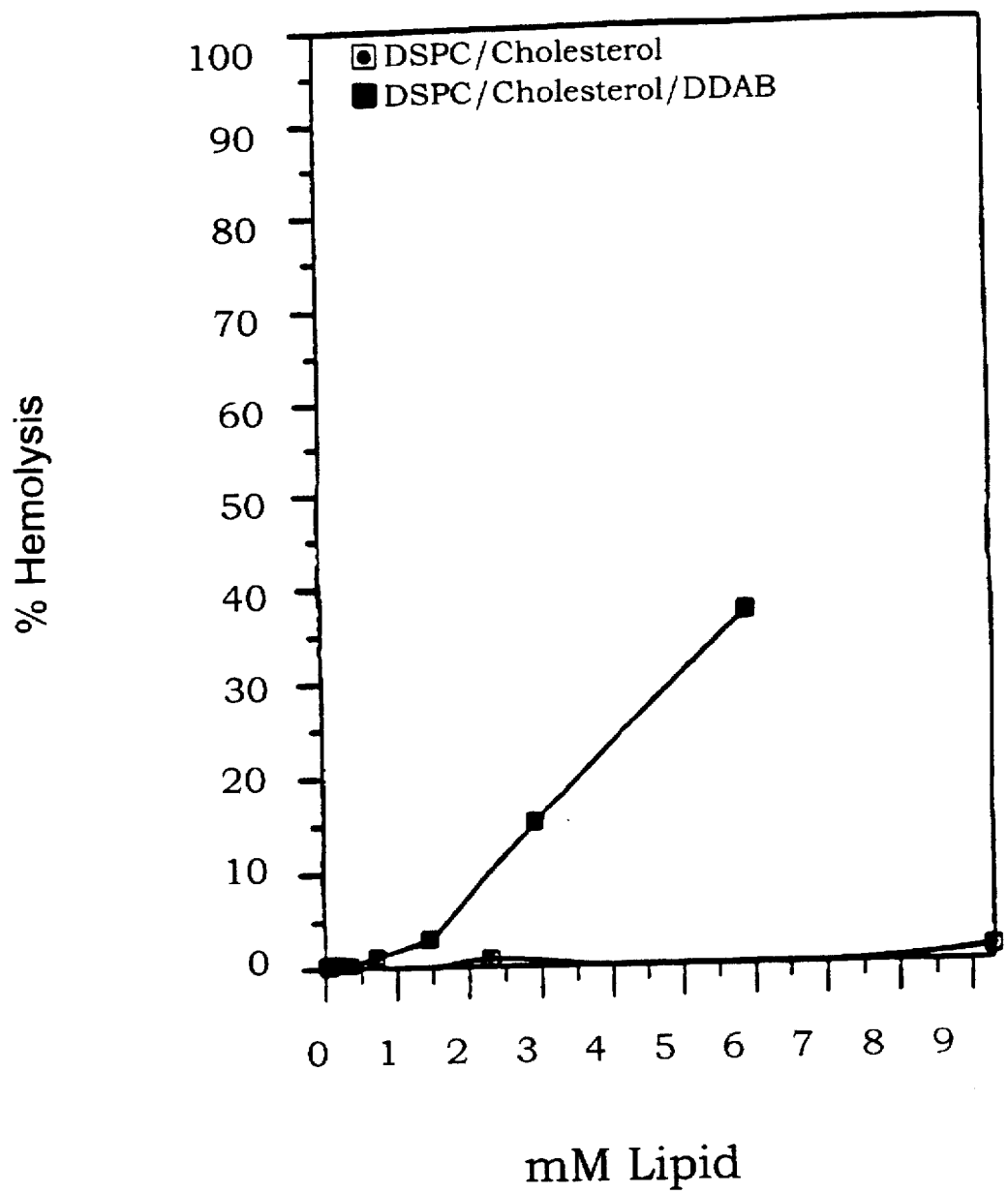

FIG. 11. Effect of Different Lipids on Red Blood Cell Hemolysis. DSPC/Chol and DSPC/Chol/DDAB liposomes were prepared and used in hemolysis assays to measure the effect of the indicated lipids on RBC hemolysis. The results are presented as the percent hemolysis (relative to zero and one hundred percent hemolysis controls) induced at various lipid concentrations in the RBC samples.

Figure 12:
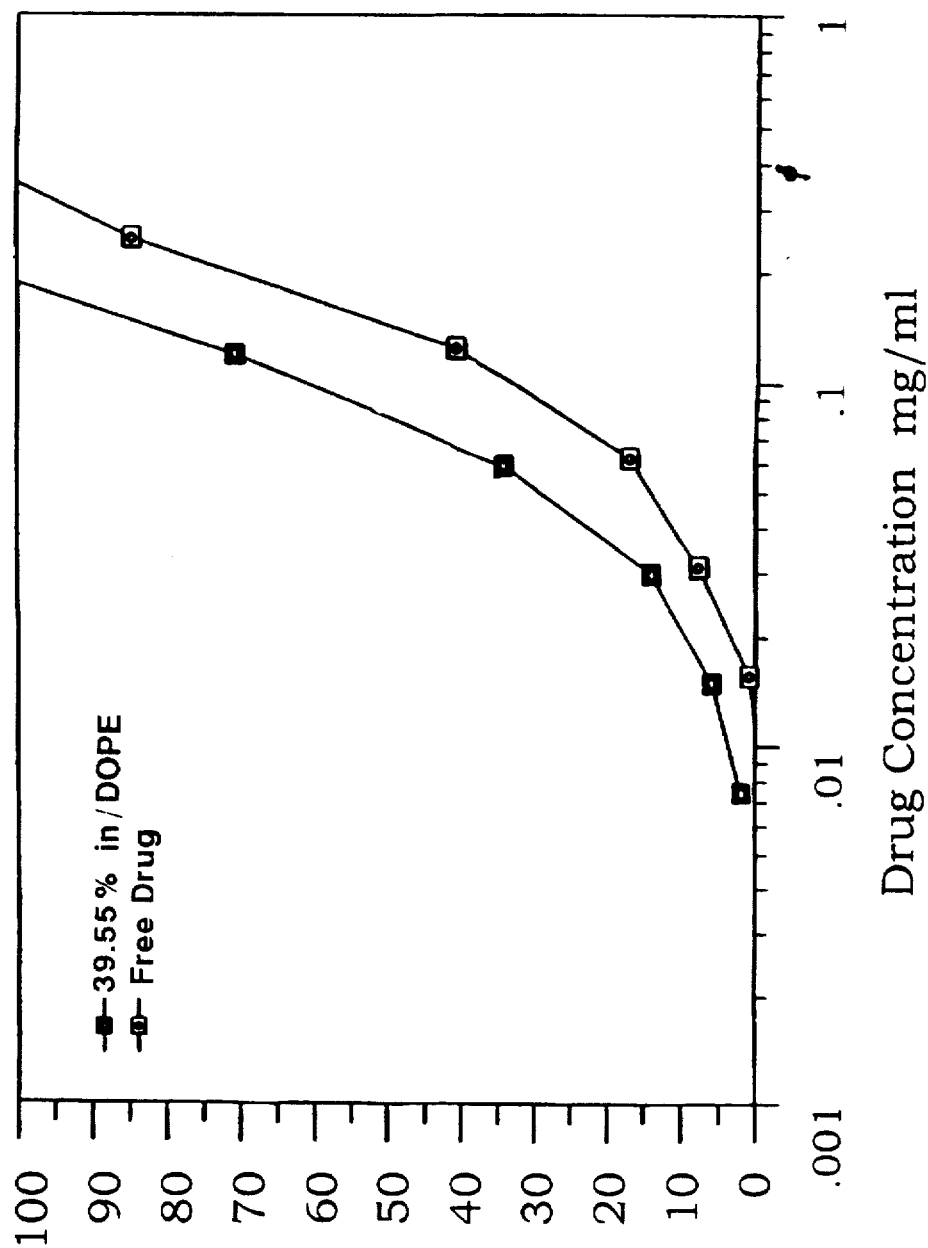

FIG. 12. Hemolytic Activity of Indolicidin/DOPE Liposomes. Indolicidin /DOPE liposomes were prepared and used in hemolysis assays. The results are presented as the percent hemolysis (relative to zero and one hundred percent hemolysis controls) induced at various lipid concentrations.

Figure 13:
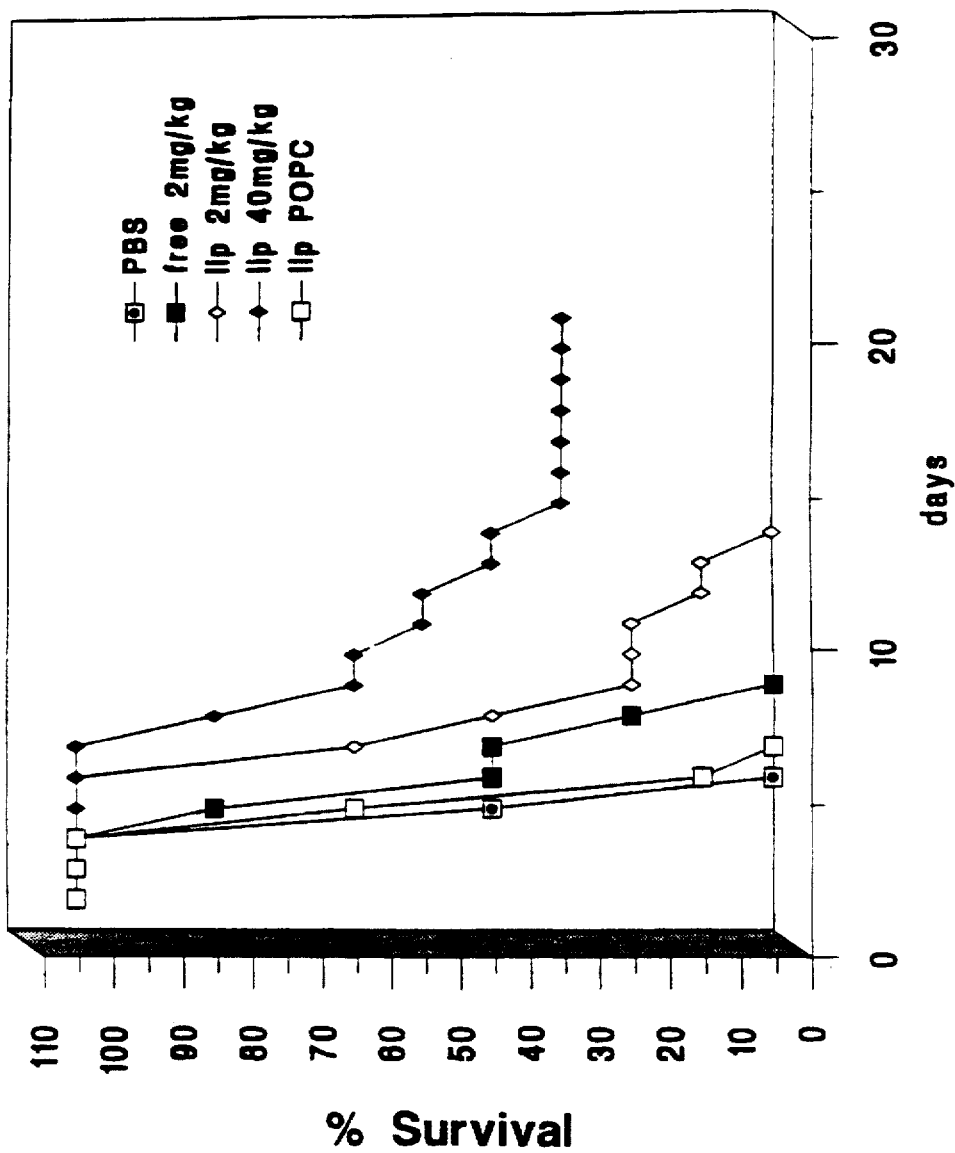

FIG. 13. Cytotoxicity of free versus liposomal indolicidin. The specific inhibition of in vitro proliferation of CHO/K1 cells by free indolicidin at increasing concentrations (µg/ml), empty liposomes and liposomal indolicidin at increasing indolicidin concentrations (µg/ml) (horizontal axis) was measured by a standard thymidine incorporation assay (cpm$\times 10^3$, vertical axis).

Figure 14:
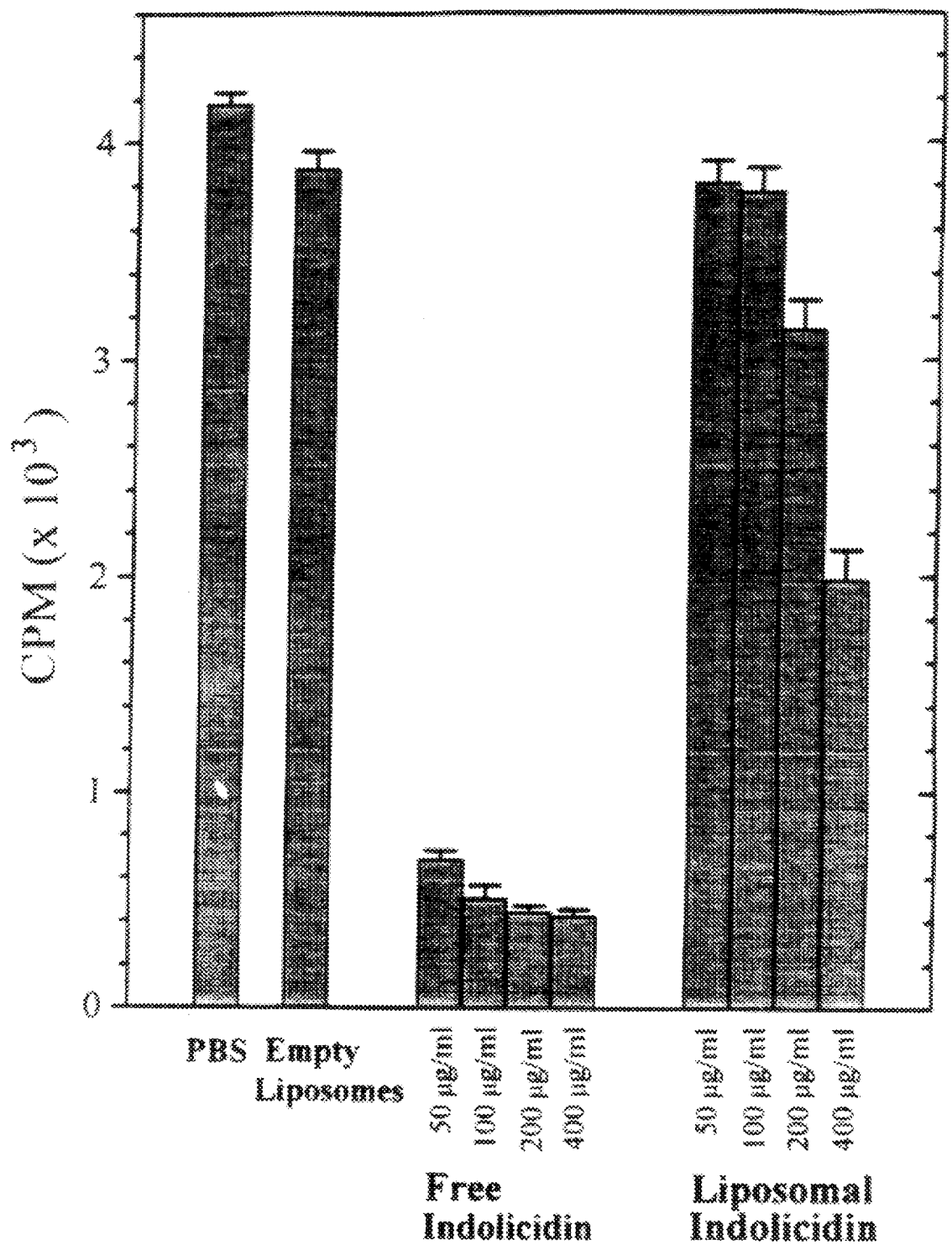

FIG. 14. Therapeutic Efficacy of Free and Liposomal Indolicidin Against Aspergillus Infections in Mice. Balb/c mice were each infected with $2\times10^7$ A. fumigatus spores and were then injected with either PBS buffer, free indolicidin or liposomal indolicidin. The animals' survival was monitored over a period of fifteen days. Percent survival (vertical axis) is plotted against time in days (horizontal axis).

DETAILED DESCRIPTION OF THE INVENTION

This invention provides a liposome comprising a lipid bilayer, an aqueous compartment and a defensin, wherein the defensin is a neutralized defensin. Defensins are microbicidal and/or tumoricidal cytotoxic proteins, polypeptides or peptides found in, or secreted by, specialized animal host defense system cells. The proteins can be cytotoxic to infectious organisms, e.g., bacteria, fungi and parasites, as well as abnormal, e.g., cancerous, or senescent host cells, and have been found to inactivate enveloped viruses. The proteins have been found in mammals such as humans, cows, guinea pigs, rabbits and rats. They have also been obtained from non-mammalian animals such as frogs, insects and sharks.

"Prototypical mammalian defensins" are variably cationic proteins found in the cytoplasmic granules of mammalian phagocytes. These defensins typically comprise between about 29 and 34 amino acids, have a conserved pattern of six cysteine residues and are amphiphilic. The prototypical mammalian defensins include human neutrophil proteins 1,2 and 3 (HNP-1, HNP-2 and HNP-3), as well as rabbit, rat and guinea pig neutrophil proteins.

Additional defensins, including other mammalian defensins as well as those derived from non-mammalian animals, have similar cytotoxic activities while differing in sequence and/or structure from this prototypical pattern. The beta-defensins, for example, can have a similar array of cytotoxic activities to those of the prototypical mammalian defensins and can also be obtained from bovine neutrophils, but have different consensus amino acid sequences and three-dimensional structures. Indolicidin is a thirteen amino acid microbicidal, tumoricidal cytotoxic protein which can also be isolated from bovine neutrophils. Indolicidin has comparable cytotoxic activity to the prototypical mammalian defensins, but is smaller and lacks their six conserved cysteines. Insect defensins are also cationic, have a pattern of six conserved cysteines, are highly amphiphilic and are cytotoxic, although they differ from the prototypical mammalian defensins in size and three-dimensional structure. Magainins are cationic, amphiphilic microbicidal host defense system proteins originally obtained from frogs. Furthermore, defensins have also been found in sharks.

Accordingly, the term "defensin" as used herein means a microbicidal and/or tumoricidal protein, peptide or polypeptide which is a component of an animal's host defense system against infectious, abnormal or senescent cells and which can be found in, or can be secreted by, cells of the animal's host defense system. "Defensins" include, but are not limited to, "prototypical mammalian defensins," beta-defensins, indolicidin, magainins and insect defensins, as well as other animal host defense system proteins, e.g., those derived from sharks. The term "defensins" includes such proteins whether they are isolated from animal cells or are synthetically produced, and also includes variants which substantially retain the cytotoxic activities of their parent proteins, but whose sequences have been altered by insertion or deletion of one or more amino acids. Presently, the preferred defensin for use in the liposomal formulations of this invention is indolicidin.

A "neutralized" defensin is a defensin which is associated with a liposome and which is inhibited from disrupting the bilayer organization of the liposome by one or more of the vesicle's components. The term "associated" describes defensins which are contained in an aqueous compartment of the liposome or defensins which are contained in a lipid bilayer of the liposome. Neutralized defensins generally do not substantially leak from liposomes, but do retain their cytotoxic activities, i.e., they are capable of disrupting a target's bilayer organization when exposed to the target. Defensins are preferably neutralized by inhibiting their interaction with lipid bilayers. Vesicle components which inhibit defensin-bilayer interaction, e.g., by increasing bilayer rigidity to inhibit defensin insertion, or by inducing defensins to aggregate in an aqueous compartment such that they generally do not then insert into the bilayer, can neutralize defensins. Alternatively, defensins can be neutralized by inducing their stable insertion into lipid bilayers. Vesicle components can induce stable defensin insertion, for example, by forming favorable Van der Waal's type interactions with the hydrophobic portions of the proteins, by allowing space for the proteins in the bilayer interior or by forming favorable electrostatic interactions with the defensins. Preferred defensin-bilayer interactions result in the least disturbance to the structural organization of the bilayer. Changes in bilayer organization can be measured by measuring changes in the order parameter of the bilayer as it is perturbed, e.g., by the addition of a defensin to the bilayer. Order parameters, which can be measured by methods well known to those of ordinary skill in the art, measures the degree to which the orientation of the carbon-carbon bonds of the lipids making up the bilayer are correlated with the normal to the bilayer-aqueous environment interface (see, e.g., S. Gruner, *Nonlamellar Lipid Phases*, in: *The Structure of Biological Membranes* (P. Yeagle, ed.), CRC Press, Inc., Boca Raton (1992), pp. 222-223, the contents of which are incorporated herein by reference). Perturbation to bilayer organization can be expected to decrease the correlation. Preferred release-inhibiting lipids which induce favorable interactions with defensins are those which exhibit the least change in the order parameter, the least disturbance to bilayer organization.

Liposomes are self-assembling structures comprising one or more lipid bilayers surrounding an internal aqueous volume. Lipid bilayers comprise two opposing monolayers of amphipathic lipid molecules, each of which comprises a polar (hydrophilic) headgroup adjacent to an internal, or external, aqueous phase, and hydrophobic acyl chains arrayed in the bilayer interior. The headgroup can be phosphate, sulfate, amino or other suitable polar moities, but are preferably phosphate groups; the acyl chains are typically 14–24 carbon atoms in length and may have one or more double bonds, i.e., the acyl chains may be saturated or unsaturated. The formation of stable lipid bilayers reflects an energy balance of hydrophobic effects from the interaction of acyl chains and the surrounding aqueous environment, steric packing constraints on the acyl chains, attractive and repulsive interactions at the interface of the bilayer with the aqueous environment, curvature elasticity of the bilayer, and the like.

Liposomes can have one lipid bilayer, i.e., they can be unilamellar, or multiple bilayers, i.e., they can be multilamellar (MLVs). Unilamellar vesicles can be small (SLTs) or large unilamellar vesicles (LUVs), liposomes with average diameters of greater than about 50 nm.

MLVs can be prepared by dissolving lipids in an organic solvent, evaporating the solvent and then adding an aqueous medium to the resultant lipid film (see, e.g., Bangham, J. Mol. Biol. 13:238 (1965)). Cullis et al. (U.S. Pat. No. 4,975,282), Lenk et al. (U.S. Pat. Nos. 4,522,803, 5,030,453 and 5,169,637) and Fountain et al. (U.S. Pat. No. 4,588,578) disclose methods for producing multilamellar liposomes wherein the liposomes contain a solute entrapped in their aqueous compartments and wherein the concentration of the solute in each of the compartments is substantially equal, i.e., the liposomes have substantially equal interlamellar solute distribution.

Unilamellar vesicles can be produced from MLVs by sonication (see Pahadjopoulos et al., Biochem. Biophys. Acta. 135:624 (1968)) or extrusion under pressure through filters (see Cullis et al., U.S. Pat. No. 5,008,050 and Loughrey et al., U.S. Pat. No. 5,059,421). These disclosures are incorporated herein by reference to describe the state of the art with respect to liposome preparation.

The liposome of this invention can be unilamellar or multilamellar, but is preferably multilamellar. Multiple lipid bilayers present a greater number of barriers to defensin release from liposomes. The multilamellar liposome can be an ordinary MLV, that is, an MLV produced by a process similar to that of Bangham et al. (J. Mol. Biol. 13:238 —dissolve amphipathic lipid(s) in an organic solvent, evaporate the solvent and then rehydrate the dried lipids with an aqueous medium). Such MLVs can be further processed. For example, POPC, indolicidin-containing liposomes can be prepared by preparing a mixture of indolicidin and POPC in one or more organic solvents (e.g., ethanol, methanol and chloroform), evaporating the organic solvent and hydrating the dried lipids with an aqueous buffer. The resultant liposomes are ordinary MLVs and can be extruded through filters of a defined pore size (e.g., five microns), to reduce their lamellarity and homogenize their size, according to the procedures of Cullis et al. (U.S. Pat. No. 5,008, 050) and Loughrey et al. (U.S. Pat. No. 5,059,421). However, the multilamellar liposome of this invention preferably contains a solute entrapped in its aqueous compartments, wherein the concentration of the solute in each of the aqueous compartments is substantially equal, i.e., the multilamellar liposome has substantially equal interlamellar solute distribution. The liposome can, for example, be prepared with DSPC and cholesterol and can be more osmotically stable than an ordinary MLV.

The liposome of this invention can further comprise a release-inhibiting lipid, i.e., a lipid which inhibits release of defensins from liposomes. A "release-inhibiting lipid" can be a lipid which inhibits defensin-bilayer interactions such that the proteins generally cannot insert themselves into lipid bilayers, and thereby generally do not disrupt bilayer organization. Such lipids can inhibit defensin-bilayer interaction, for example, by way of charges on the headgroups which form electrostatic repulsions with charged groups on defensins, and by increasing membrane rigidity, or otherwise limiting the ability of hydrophobic defensin domains to interact favorably with hydrophobic acyl chains in bilayer interiors. Preferably, the release-inhibiting lipid of this invention is a lipid which inhibits defensin-bilayer interactions. The presently preferred such release-inhibiting lipid comprises DSPC plus cholesterol, desirably in a 3:2 molar ratio of DSPC to cholesterol. Alternatively, a release-inhibiting lipid can be a lipid which can interact favorably with a defensin in a lipid bilayer. Release-inhibiting lipids can interact with defensins by way of favorable Van der Waal's type interactions between the hydrophobic acyl chains and hydrophobic domains of defensins; release-inhibiting lipids can also form covalent bonds with defensins. Electrostatic interactions can be formed between charged lipid headgroups and charged defensins, with the hydrophobic portion of the defensin remaining in the bilayer interior. Such "favorable" interactions result in the least disturbance of the bilayer organization, which minimizes the potential for defensin release. Release-inhibiting lipids can also establish favorable steric conditions for insertion of the hydrophobic domains of defensins into the bilayer interior. Furthermore, release-inhibiting lipids can induce a defensin to insert its hydrophobic domain into a lipid bilayer such that the defensin does not form pores in the bilayer. Presently preferred release-inhibiting lipids which interact favorably with defensins are 1-palmitoyl-2-oleoyl phosphatidylcholine (POPC) or dioleoyl phosphatidylcholine (DOPC).

Accordingly, in one embodiment of the invention, the defensin comprises indolicidin and the release-inhibiting lipid comprises POPC. Typically, the indolicidin/POPC liposomes comprise at least about 0.5 mole percent indolicidin and at most about 99.5 mole percent POPC; desirably, the liposomes comprise about 5 mole percent indolicidin and about 95 mole percent POPC. In another embodiment of the invention, the defensin comprises indolicidin and the release-inhibiting lipid comprises DOPC. Typically, the liposome comprises at least about 0.5 mole percent indolicidin and at most about 99.5 mole percent DOPC. As used herein, "mole percent" of a lipid or protein means the number of moles of the lipid or protein divided by the total number of moles present (i.e., mole percent of A=(A)/(A+B)).

In a presently preferred embodiment of the invention, the defensin comprises indolicidin and the release-inhibiting lipid comprises DSPC plus cholesterol, the DSPC and cholesterol preferably being present in a molar ratio of about 3 to 2 DSPC:cholesterol. Typically, the liposome comprises at least about 0.5 mole percent indolicidin and at most about 99.5 mole percent DSPC and cholesterol, desirably, about 20 mole percent indolicidin and about 80 mole percent DSPC plus cholesterol.

The liposome provided herein can further comprise a release-inhibiting buffer. As used herein, a "release-inhibiting buffer" is an aqueous solution which inhibits or prevents release of a defensin entrapped in a liposome. Such buffers inhibit defensin release by inhibiting the proteins from disrupting lipid bilayers, preferably, by inhibiting defensin interaction with the bilayers. Defensin-bilayer interaction may be inhibited by inducing defensin molecules to interact, or cross-link, with each other such that the resulting aggregates generally do not insert themselves into lipid bilayers. Defensins can be induced to form complexes by placing them in anionic, preferably polyanionic, aqueous solutions such that various defensin molecules and anions form electrostatic interactions. For example, indolicidin can be precipitated as a complex by placing it in a 50 mM citrate solution. Precipitation is facilitated by electrostatic pairing between positive charges on the indolicidin (five total per molecule) and negative charges on the citrate (three total per molecule at pH 7), and is indicative of the cross-linking of protein molecules. The cross-linked, precipitated defensin complexes can be entrapped in liposomes by adding an aqueous suspension of the complexes to the lipids with which the vesicles are prepared. Defensin complexes can also be entrapped in liposomes by forming vesicles such that they contain the defensin or polyanion, but not both, and are impermeable to the entrapped species while being permeable to the unentrapped. When the unentrapped, permeable species is introduced to the external environment surrounding the liposome, a precipitate forms in the vesicle as the permeable species migrates into its interior and electrostatic interactions induce defensin aggregation.

Liposomal defensins provided herein can further comprise a second bioactive agent, i.e., a bioactive agent in addition to the defensin. "Bioactive agent" as used herein denotes any compound or composition of matter having biological activity in animals, e.g., humans. Bioactive agents include, but are not limited to: antiviral, antibacterial, antifungal, antiparasitic, antimetabolic, antiglaucomic, anti-inflammatory or antineoplastic compounds, sterols, carbohydrates, amino acids, peptides, proteins, immunoglobulins, immunomodulators, dyes, toxins, enzymes, hormones, neurotransmitters, glycoproteins, radiolabels, radiopaque compounds, fluorescent compounds, cell receptor proteins, cell receptor ligands, mydriatic compounds, bronchodilators, local anesthetics, growth promoting agents, regenerative agents and the like. This second bioactive agent may be an additional defensin.

The liposome provided herein can further comprise a headgroup-modified lipid. Liposomes are cleared from an animal's body by way of its reticuloendothelial system (RES) which consists of fixed and circulating macrophages. Avoiding RES clearance allows liposomes to remain in the circulation longer, meaning that less of the drug need be administered to achieve desired serum levels. Enhanced circulation times also allow targeting of liposomes to non-RES containing tissues. Liposomal surfaces become coated with serum proteins when administered to animals. Rates of clearance by the RES can be related to the rate and level of such protein coating; accordingly, clearance can be inhibited by modifying the outer surface of liposomes such that binding of serum proteins is generally inhibited. This can be accomplished by minimizing or shielding negative surface charges, which can promote protein binding, or by otherwise presenting a steric hindrance to the binding of serum proteins.

Effective surface modification, that is, alterations to the outer surfaces of liposomes which result in inhibition of RES uptake, can be accomplished by incorporating headgroup-modified lipids into liposomal bilayers. "Headgroup-modified lipids" as used herein are amphipathic lipids whose polar headgroups have been derivatized by attachment thereto of a chemical moiety, e.g., polyethylene glycol, a polyalkyl ether, a ganglioside, an organic dicarboxylic acid or the like, which can inhibit the binding of serum proteins to liposomes such that the pharmacokinetic behavior of the vesicles in the circulatory systems of animals is altered (see, e.g., Blume et al., Biochim. Biophys. Acta. 1149:180 (1993); Gabizon et al., Pharm. Res. 10(5):703 (1993); Park et al. Biochim. Biophys Acta. 1108: 257 (1992); Woodle et al., U.S. Pat. No. 5,013,556; Allen et al., U.S. Pat. Nos. 4,837,028 and 4,920,016 (PCT Publication No. WO 88/04924 (Jul. 14, 1988)); the contents of these disclosures are incorporated herein by reference). The liposome provided by this invention can further comprise such a headgroup-modified lipid. The amount of the headgroup-modified lipid incorporated into the liposome depends upon a number of factors well known to the ordinarily skilled artisan, or within his purview to determine without undue experimentation. These include, but are not limited to: the type of lipid and the type of headgroup modification; the type and size of the liposome; and the intended therapeutic use of the liposomal defensin formulation. Typically, the concentration of the headgroup-modified lipid in the liposome is at least about five mole percent, desirably, about ten mole percent.

The lipid bilayer of the liposome of this invention can comprise an ionizable lipid. Ionizable lipids placed in an environment with the appropriate pH will bear one or more positive or negative charges. Interactions between proteins entrapped in liposomes and lipid components of the liposomes bearing the same type of charge can lead to electrostatic repulsions between the protein and the lipid; such electrostatic repulsions can inhibit release of the proteins from the liposomes.

Defensins are generally cationic proteins. Accordingly, inclusion of an ionizable, cationic lipid in a liposomal bilayer can induce electrostatic repulsions with a defensin and thereby inhibit release of the defensin from the liposome. The amount of an ionizable lipid to incorporate into a lipid bilayer is any amount which can prevent defensin-bilayer interaction and thereby inhibit defensin release, and which is otherwise compatible with liposome preparation, stability and use. The amount will depend upon a number of factors well known to the ordinarily skilled artisan, or within his purview to determine without undue experimentation, given this invention. These factors include, but are not limited to: the type of lipid and the amount of charge per molecule, the defensin and the type of liposome used. Typically, the amount of the ionizable lipid incorporated into a lipid bilayer is about five mole percent of the lipid in the bilayer, desirably, about ten mole percent.

Preferably, greater than about fifty percent of the ionizable lipid present in the outermost lipid bilayer of the liposome is present in the inner monolayer of the outermost lipid bilayer. Lipid bilayers comprise two opposing monolayers of amphipathic lipid molecules, an inner and an outer monolayer. The outermost lipid bilayer of a liposome is the lipid bilayer the outer monolayer of which is adjacent to the external environment surrounding the liposome. Accumulation of an ionizable lipid in the inner monolayer of a lipid bilayer will maximize electrostatic repulsive forces with ionizable proteins entrapped in the aqueous compartment surrounded by the bilayer, while minimizing exposure of the charged lipids to the external environment. Ionizable lipids can be accumulated in the inner monolayer of a lipid bilayer by establishing an electrochemical potential gradient, e.g., a proton gradient, across the bilayer according to the procedure of Hope et al. (U.S. Pat. No. 5,204,112, (PCT Publication No. WO 87/07530 (Dec. 17, 1987)) and U.S. Pat. No. 5,252,263). Presently, it is preferred that the ionizable lipid incorporated into the liposome of this invention is DPDAP (1,2-dipalmitoyl-3-(N,N-Dimethylamino)-propane.

This invention further provides a dehydrated liposome comprising a defensin, wherein the defensin is a neutralized defensin. Liposomal dehydration enables the vesicles to be stored for extended periods of time; they can then be reconstituted on an as-needed basis. Liposomes can be dehydrated, with freezing, using standard freeze-drying equipment, or its equivalents. Lyophilization is preferably carried out after incorporating one or more protective sugars into liposome preparations in accordance with the procedures described in Schneider et al. (U.S. Pat. No. 4,229,360) and Janoff et al., (U.S. Pat. No. 4,880,635 (PCT Publication No. WO 86/01103 (Feb. 27, 1986)), the contents of which are incorporated herein by reference). The protective sugar can be omitted if the dehydration is conducted without freezing and sufficient water is left remaining in the liposomal preparation to maintain the integrity of a substantial portion of the liposomal bilayers through the dehydration-rehydration process.

This invention also provides a pharmaceutical composition comprising a pharmaceutically acceptable carrier and a liposome comprising a lipid bilayer, an aqueous compartment and a defensin, wherein the defensin is a neutralized defensin. "Pharmaceutically acceptable carrier" as used herein means any of the standard carriers, diluents, excipients and the like generally intended for use in connection with the administration of biologically active agents to animals. Such carriers are well known in the art and are generally chosen with regards to a number of factors, such as the particular drug being used and the intended route of administration, which are well understood by the ordinarily skilled artisan, or are within his purview to determine. Suitable carriers include, but are not limited to salt solutions such as physiological saline, aqueous buffered solutions, and the like. The pharmaceutical composition can further comprise auxiliary agents such as preservatives, anti-oxidants and the like in amounts, and for reasons, well known to the ordinarily skilled artisan. The pharmaceutical composition can be provided as a unit dosage form, which can comprise an anti-infection effective or anticancer effective amount of the pharmaceutical composition.

The pharmaceutical compositions provided herein may be used in methods of treating or preventing an infection in an animal, e.g., a mammal, preferably a human and most preferably, humans whose immune systems have been compromised, e.g., by viruses such as HIV, by chemotherapy or for organ transplantation. These methods comprise administering to the animal an anti-infection effective amount of the pharmaceutical composition used. The infection may be a viral, bacterial, fungal, parasitic or other type of microbial infection which is sensitive to a defensin. The responsiveness of infectious organisms to various anti-infection agents can be determined by readily available methods well known to those skilled in the art, e.g., by microbial sensitivity tests. Fungal infections sensitive to a defensin, such as Cryptococcus and Aspergillus infections in animals, are presently preferred objects of treatment with the methods of this invention. Accordingly, in presently preferred embodiments of the invention, immunocompromised humans are treated for a Cryptococcus infection or an Aspergillus infection with a liposomal defensin provided herein.

Defensin action is generally neither species nor cell-type specific. That is, defensins from one animal can be active in another animal and can induce cytolysis of the cells of the other animal. A particular defensin can also be active against a variety of microbes and cell types and is generally not limited to action against specific cells. Accordingly, the practice of this invention contemplates the administration of an anti-infection effective amount of a defensin originally obtained from one type of animal to another type of animal, for a variety of microbial infections or cancers. For example, indolicidin, derived from bovine neutrophils, can be used to treat humans.

Methods of administering pharmaceutical compositions to animals include intravenous, intra-arterial, intra-ocular, intraperitoneal, intramuscular, intranasal, intravaginal, subcutaneous, rectal and topical administration. The mode of administration chosen for a particular pharmaceutical composition will depend upon a number of factors well known to the ordinarily skilled artisan or well within his purview to determine without undue experimentation. These include, but are not limited to: the treatment subject and its age, size and general condition; the active agent being administered; and the disease, disorder or condition being treated. Presently, the preferred route of administration comprises intravenous administration.

"Anti-infection effective amount" of a pharmaceutical composition means any amount of a pharmaceutical composition that is effective to inhibit or prevent the establishment, growth or spread of an infection sensitive to a defensin. Typically, the anti-infection effective of the pharmaceutical composition provided herein is an amount containing between 1 mg of a liposomal defensin per kg of the body weight of the animal to which the composition is administered to about 1000 mg per kg of body weight; desirably, the anti-infection effective amount of the pharmaceutical composition contains about 10 mg of a liposomal defensin per kg of body weight to about 200 mg per kg. Within this range, the amount or dose of the pharmaceutical composition given a particular animal will depend upon a number of factors well known to the ordinarily skilled artisan, or within his purview to determine without undue experimentation. These include, but are not limited to: the type of microbial infection and the stage of its progression; the subject and its age, size and general condition; and the preferred route of administration of the pharmaceutical composition. The particular amount of the pharmaceutical composition administered for the particular disease, disorder or condition indicated may be determined by methods well known to the ordinarily skilled artisan, e.g., by dose ranging trials.

Further provided herein is a method of treating an animal, e.g. a mammal and preferably, a human, afflicted with a cancer responsive to a defensin, e.g., a leukemia or a lymphoma. This method comprises administering to the animal an anticancer effective amount of the pharmaceutical composition provided herein. For the purposes of this invention, an "anticancer effective amount" of a pharmaceutical composition is any amount of the pharmaceutical composition effective to inhibit the establishment, growth or metastasis of a tumor in an animal. Typically, the anticancer effective amount of the pharmaceutical composition is an amount containing between 1 mg of the liposomal defensin per kg of the body weight of the animal to which the composition is administered to about 1000 mg per kg of body weight; desirably, the anticancer effective amount of the pharmaceutical composition contains about 10 mg of a liposomal defensin per kg of body weight to about 200 mg per kg. Within this range, the amount or dose of the pharmaceutical composition given a particular animal will depend upon a number of factors well known to the ordinarily skilled artisan or within his purview to determine without undue experimentation. These include, but are not limited to: the type of microbial infection and the stage of its progression; the subject and its age, size and general condition; and the preferred route of administration. The particular amount of the pharmaceutical composition administered for the particular disease, disorder or condition indicated may be determined by methods well known to the ordinarily skilled artisan, e.g., by dose ranging trials.

This invention is illustrated by the following Examples. However, those of ordinary skill in the art will readily understand that these Examples are merely descriptive of the invention as defined in the claims which follow thereafter.

EXAMPLES

Example 1

Light Scattering of Indolicidin

Indolicidin was dissolved at various concentrations in 10 mM HEPES buffer (pH 7.5), containing 150 mM NaCl. Samples were placed in fluorescence cuvettes and light scattering at 500 nm (excitation wavelength was measured in the fluorimeter, at a 90 degree angle.

Figure 1:
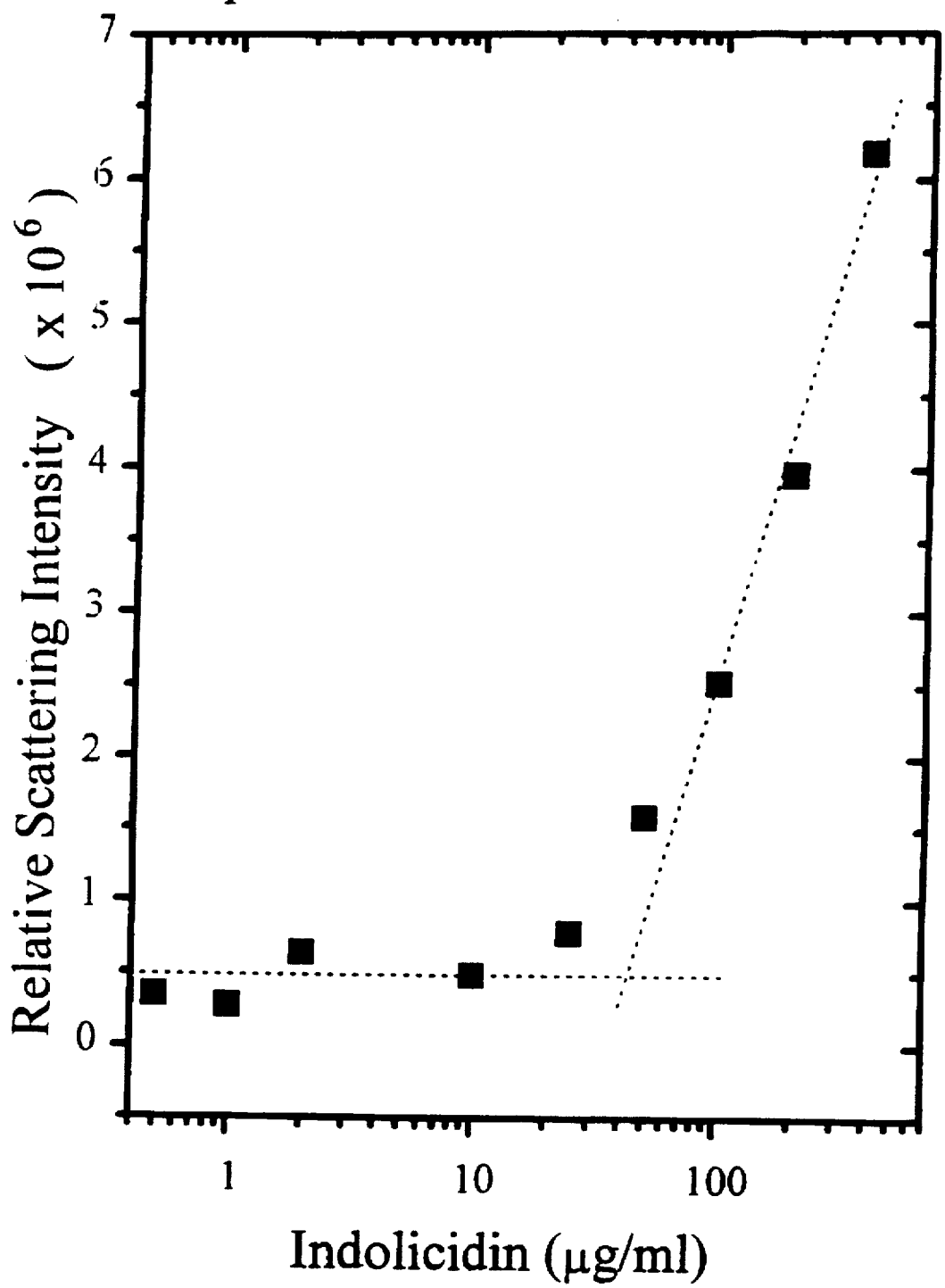
FIG. 1. Right Angle Light Scattering of Aqueous Indolicidin. Indolicidin was dissolved at various concentrations in buffer solutions containing 10 mM HEPES and 150 mM NaCl, pH 7.5. Samples were placed in fluorescence cuvettes and the scattering of light at 500 nm wavelengths (excitation wavelength) was measured in the fluorimeter at an angle of 90 degrees. Buffer alone (no indolicidin) had a relative light scattering of $0.4 \times 10^6$. The vertical axis is a measure of relative scattering intensity; the horizontal axis sets forth the indolicidin concentration (µg/ml).

The results (see FIG. 1) indicate that indolicidin self-associates in solution at concentrations of about 30 µg/ml and greater. Such self-association is favorable because it can minimize exposure of non-polar regions of indolicidin to water molecules.

Example 2

Fluorescence of Aqueous Indolicidin

Figure 2:
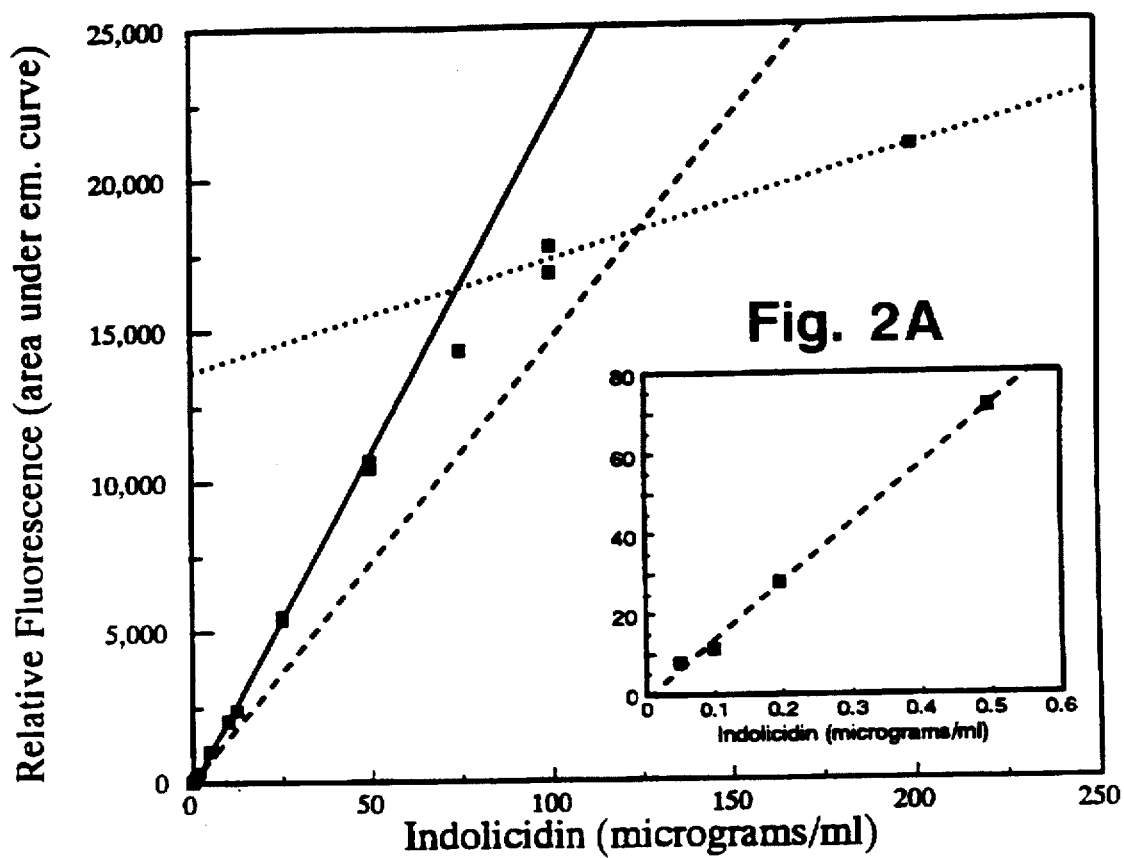
FIG. 2. Fluorescence of aqueous indolicidin. Indolicidin was dissolved in 10 mM HEPES buffer, pH 7.5 containing 150 mM NaCl. The excitation wavelength was set at 285 nm, and emission wavelengths were scanned from 325 nm to 450 nm. The area under the emission curve (vertical axis) was plotted against the indolicidin concentration (µg/ml) (horizontal axis). The inset in the figure shows the trend below indolicidin concentrations of about 5 µg/ml. The dotted line representing that slope is also shown in larger profile. Three different slopes are evident. Slit widths were changed between lower and higher concentrations; intermediate concentrations were examined at both slit widths to ensure proper normalization.

Indolicidin was dissolved in pH 7.5 HEPES buffer (10 mM HEPES, 150 mM NaCl); the resulting solutions were placed in fluorescence cuvettes. The excitation wavelength was set at 285 nm; emission wavelengths were scanned from 325 nm to 450 nm. The area under the emission curve was plotted against the indolicidin concentration (see FIG. 2). Slit widths were changed between higher and lower concentrations; intermediary concentrations were examined at both slit widths to ensure proper normalization.

The results show that fluorescence of indolicidin in aqueous solution increased linearly with indolicidin concentration up to 0.5 µg/ml, but then deviated to a steeper slope between concentrations of 0.5 µg/ml and 50 µg/ml. Above 50 µg/ml, the slope decreased. These deviations reflect changes in the intermolecular self-associations of indolicidin molecules at different indolicidin concentrations.

Example 3

Preparation of Indolicidin/POPC Unilamellar Liposomes

An indolicidin/POPC solution (1-palmitoyl-2-oleoyl phosphatidylcholine; 0.085:1 (w/w) indolicidin/POPC) was dried on a rotary evaporator, and then rehydrated with buffer (10 mM HEPES, 150 mM NaCl, pH 7.4) so as to form a suspension of multilamellar liposomes. The liposomes were then extruded through a filter with 100 nm pores to produce large unilamellar vesicles (LUVs; see Cullis et al., U.S. Pat. No. 5,008,050 and Loughrey et al., U.S. Pat. No. 5,059,421, the contents of which are incorporated herein by reference).

Example 4

Preparation of DSPC/Chol Multilamellar Liposomes

Indolicidin (66 mg in ethanol), distearoyl phosphatidylcholine (DSPC; 56 mg in chloroform) and cholesterol (Chol; 19 mg in chloroform) were mixed, and 3 ml of buffer (10 mM HEPES, 150 mM NaCl, pH 7.4) was then added. The resulting mixture was brought to near dryness in a round-bottom flask, and the dried lipids were then rehydrated with methanol and 1 ml of water so as to form a suspension of multilamellar liposomes (MLVs). The MLV suspension was placed on a vacuum rotary evaporator and dried at 45 deg. Celsius, with full vacuum, to a paste. The sample was then cooled, and 10 ml of HEPES buffer added. The resulting solution was transferred to a 30 ml tube and vortexed. This preparation was centrifuged and spun at 12,000 g for 10 minutes. The liposomes pelleted; the supernatant above the pellet was removed, and replaced with fresh buffer solution. This washing by centrifugation was repeated four additional times, for a total of five washes, with the final pellet, comprising multilamellar liposomes having substantially equal interlamellar solute distribution, being resuspended to a total volume of 1.7 ml.

Example 5
Retention of Indolicidin in Phosphatidylcholine-Containing Liposomes

Liposomes containing indolicidin and either POPC, POPC/Chol, DPPC (dipalmitoyl phosphatidylcholine) or DPPC/Chol were prepared using indolicidin/buffer solutions having 13–28 micrograms per ml of indolicidin, and lipid solutions at concentrations of 1.5–2.5 mM. The lipid solutions were dried by rotary evaporation; the indolicidin solution was added to the dried lipids so as to form a dispersion of multilamellar vesicles (MLVs). These MLVs were then subjected to seven free-thaw cycles (see Cullis et al., U.S. Pat. No. 4,975,282, the contents of which are incorporated herein by reference) so as to produce multilamellar liposomes with substantially equal interlamellar solute distribution. Unentrapped indolicidin was removed from the liposome preparations; initial and final indolicidin concentrations were measured by dissolving samples in ethanol and reading absorbances at 280 nm in a UV spectrophotometer.

Figure 3:
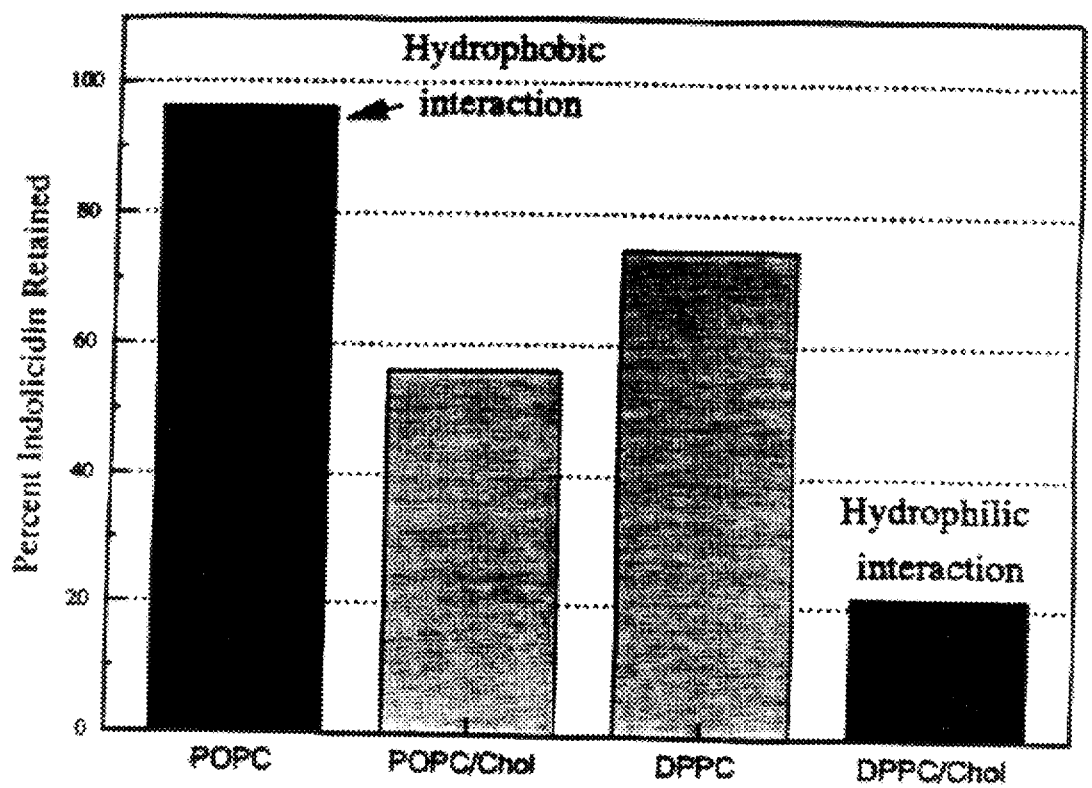
FIG. 3. Retention of Indolicidin in POPC- and DPPC-Containing Liposomes. POPC (1-palmitoyl-2-oleoyl phosphatidylcholine), POPC/Chol (cholesterol), DPPC (dipalmitoyl phosphatidylcholine) and DPPC/Chol liposomes were formed as described below and indolicidin was entrapped therein. The percentage of the indolicidin originally entrapped in the liposomes that remained therein after 48 hours was determined (according to procedures described below) and is given for each of the liposomal formulations.

The data (see FIG. 3) demonstrate that POPC-containing liposomes retained the highest percentage of indolicidin after 48 hours (about 95% of the amount originally entrapped), that DPPC-containing liposomes retained less (about 75%), POPC-Chol liposomes retained about 55% and DPPC-Chol liposomes retained about 20–30%.

Example 6
Retention of Indolicidin in DOPE-Containing Liposomes

Indolicidin (6 mg) was dissolved in 1 ml of ethanol. This was combined with a 20 mg/ml DOPE stock solution to form four samples: I:2 mg DOPE/ 1 mg indolicidin; II:2 mg DOPE/ 3 mg indolicidin; III:2 mg DOPE/6 mg indolicidin; and IV:2 mg DOPE/ 0 mg indolicidin. The samples were dried by rotoevaporation at 30 deg. C, and then rehydrated with 1 ml of HEPES buffer so as to form multilamellar liposomes. Aliquots (25 µl) were combined with 25 µl of HEPES buffer and 950 µl of ethanol in a quartz cuvette. The initial indolicidin concentration, and the concentration remaining in the vesicles after successive washes was measured by dissolving liposomal samples in ethanol and reading absorbances at 280 nm. Lipid concentrations were determined by a standard phosphate assay (see Chen et al., Anal. Chem. 28:1956 (1956)).

Figure 4:
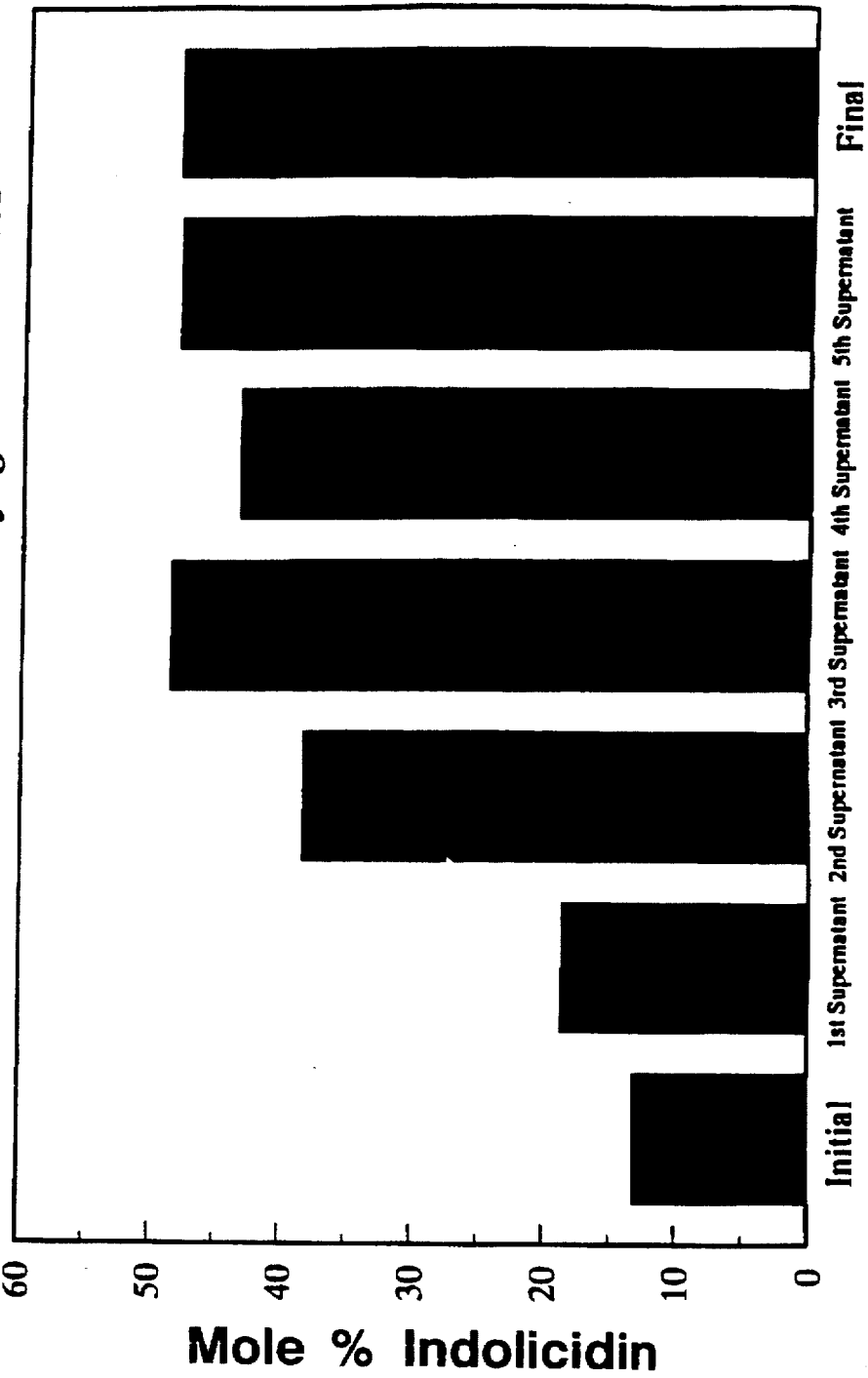
FIG. 4. Retention of Indolicidin in DOPE-Containing Liposomes. Indolicidin-containing liposomes were formed with dioleoyl phosphatidylethanolamine (DOPE) as described below. The concentration of indolicidin in the liposomes, both initially and after successive washes, is set forth.
Figure 5:
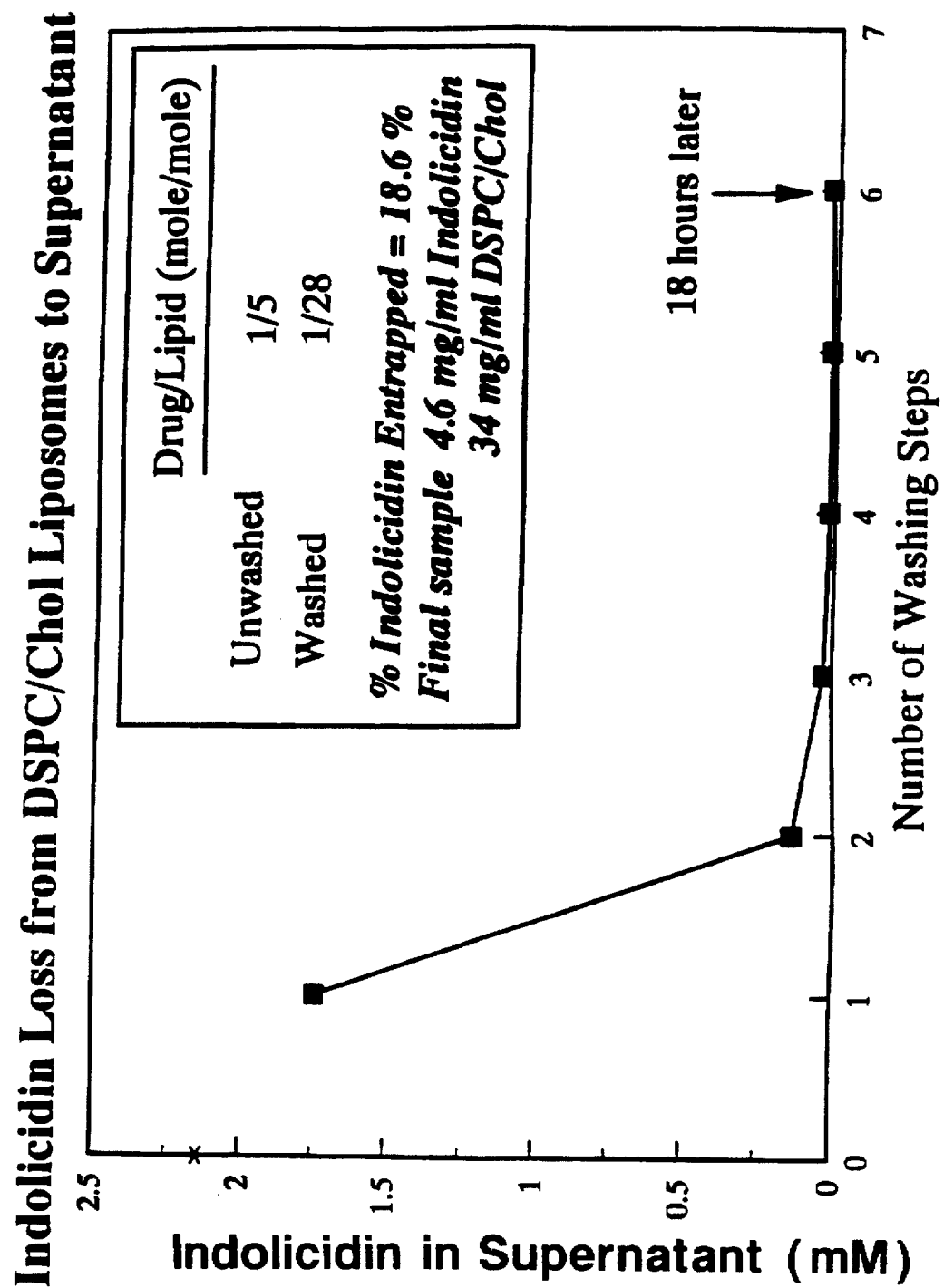
FIG. 5. Indolicidin Retention in DSPC/Chol-Containing Liposomes.

The data (see FIG. 4) shows that the mole percentage of indolicidin in the DOPE-containing liposomes was increased by washing, and reached about 50 mole percent in the final preparation.

Example 7
Effect of Indolicidin on Leakage of DSPC/Chol Liposomes

A solution of DSPC (60 mg) and cholesterol (20 mg) was dried by rotary evaporation; the dried lipids were then rehydrated with 2 ml of buffer (10 mM HEPES, 150 mM NaCl), containing 0.5 mM of the probe CAT1 (4-trimethylammmonium-2,2,6,6-tetramethylpiperidine-1-oxyl-iodide) so as to form a suspension of multilamellar liposomes containing the probe. A suspension of these vesicles was then heated for 10 min. at 65 deg. C. The sample was washed four times with HEPES buffer and resuspended in buffer to a final volume of 2 ml. A stock solution of indolicidin (20 mg/ml) was also prepared in HEPES buffer. Various amounts of this solution (see Table 1, below) were combined with an aliquot (100 µl) of the liposome preparation, with buffer then being added to bring the final volume up to 0.2 ml. Samples were microfuged, and the supernatants transferred to ESR tubes. Spectra were taken at room temperature (23 deg. C.) to determine the concentration of the probe in the supernatant samples (see Perkins et al., Biochim. Biophys. Acta. 943:103 (1988)).

The data (see Table 1, below) indicates the percent of the probe found in the supernatant, and thereby, the percent leakage from the DSPC/Chol liposomes. The results show that increasing the concentration of indolicidin in the DSPC/Chol liposomes did not significantly increase probe leakage.

TABLE 1

EFFECT OF INDOLICIDIN ON LEAKAGE OF PROBE FROM DSPC/CHOL LIPOSOMES

| µl Indolicidin | µl Lipid | µl Buffer | Mole % Indolicidin | % Probe in Supernatant | % Leakage of Probe |
|---|---|---|---|---|---|
| 0.00 | 100.00 | 100.00 | 0.00 | 4.39 | 0 |
| 3.20 | 100.00 | 96.80 | 0.42 | 6.14 | 1.75 |
| 6.30 | 100.00 | 93.70 | 0.82 | 6.14 | 1.75 |
| 12.50 | 100.00 | 87.50 | 1.61 | 5.26 | 0.87 |
| 25.00 | 100.00 | 75.00 | 3.16 | 6.14 | 1.75 |
| 50.00 | 100.00 | 50.00 | 6.16 | 7.02 | 2.63 |
| 75.00 | 100.00 | 25.00 | 8.93 | 6.14 | 1.75 |
| 100.00 | 100.00 | 0.00 | 11.59 | N/A | N/A |

N/A: data not available.

Example 8
Effect of Indolicidin on Leakage From DSPC/Chol/DDAB Liposomes

A solution of DSPC (51.6 mg), cholesterol (20.2 mg) and dimethyldioctadecyl ammonium bromide (DDAB; 8.23 mg) was dried in a round-bottom flask. The lipids were rehydrated with buffer (10 mM HEPES, 150 mM NaCl) containing 0.5 mM of the probe CAT1 so as to form a suspension of multilamellar liposomes. The suspension was heated at 65 deg. C. for 10 min and then washed twice in 10 ml of the HEPES buffer, with the final pellet comprising DSPC/Chol/DDAB multilamellar liposomes containing CAT1, being resuspended in HEPES buffer to a final volume of 2 ml. A standard phosphate assay (see Chen et al., Anal. Chem. 28:1956 (1956)) was performed to determine the amount of lipid remaining (34.12 mg). A 20 mg/ml indolicidin stock solution in HEPES buffer was also prepared.

Various amounts of this solution (see Table 2, below) were combined with an aliquot (100 µl) of the liposome suspension, the final volume of the samples being brought up to 0.2 ml with HEPES buffer. These samples were centrifuged, and aliquots of the supernatants were taken for ESR spectra determination (23 deg. C.) to measure probe leakage. A small amount of broadening agent was added to the two samples with the highest indolicidin concentrations. The results are presented in Table 2.

TABLE 2

EFFECT OF INDOLICIDIN ON LEAKAGE OF CAT1 PROBE FROM DSPC/CHOL/DDAB LIPOSOMES

| µl Indolicidin | µl Liposome Preparation | µl Buffer | Mole % Indolicidin | % Probe in Supernatant |
|---|---|---|---|---|
| 0.00 | 100.00 | 100.00 | 0.00 | 6.22 |
| 3.20 | 100.00 | 96.80 | 0.48 | 8.00 |
| 6.30 | 100.00 | 93.70 | 0.93 | 8.00 |
| 12.50 | 100.00 | 87.50 | 1.84 | 9.78 |
| 25.00 | 100.00 | 75.00 | 3.61 | 10.67 |
| 50.00 | 100.00 | 50.00 | 6.99 | 9.78 |
| 75.00 | 100.00 | 25.00 | 10.09 | 0* |
| 100.00 | 100.00 | 0.00 | 13.04 | 0* |

*Corrected for any liposomes that may have been in the supernatant.

Example 9
Entrapment of Indolicidin in DSPC/Chol- or POPC/Chol- Containing Liposomes Liposomes were formed by mixing either DSPC and cholesterol, or POPC and cholesterol, and indolicidin at indolicidin:lipid (w/w) ratios of 0.1, 0.2, 0.4 and 0.6, dissolving the mixture in organic solvent, evaporating off the solvent and then hydrating the dried preparation with 10 mM HEPES buffer so as to form multilamellar liposomes. Unentrapped indolicidin was removed by passing the liposome preparations over a column. Indolicidin concentrations were determined by dissolving liposomal preparations in ethanol and reading absorbances at 280 nm. Lipid concentrations were determined by a standard phosphate assay (see Chen et al., Anal. Chem. 28:1956 (1956)). The data is presented in Table 3, below.

TABLE 3

ENTRAPMENT OF INDOLICIDIN IN DSPC/CHOL LIPOSOMES

| Indolicidin: Lipid (w/w) | Percent Indolicidin Entrapped After Dialysis |
|---|---|
| 0.1 | 90.0 |
| 0.2 | 18.8 |
| 0.4 | 9.9 |
| 0.6 | 15.6 |

Example 10
Fluorescence of Free and Liposomal Indolicidin

Liposomes were prepared by hydrating dried preparations of POPC, POPC/Cholesterol (3:2), DPPC and DPPC/Chol (3:2) (40 mg lipid each) with 8 ml HEPES buffer (10 mM HEPES, 150 mM NaCl, pH 7.5) so as to form multilamellar vesicles. These MLVs were then extruded through 2 stacked polycarbonate filters having 0.1 µm pores, at 50 deg. C. Aliquots of each sample were diluted to a lipid concentration of 0.1 mg/ml, and fluorescence spectra were taken. Fluorescence profiles were also taken after indolicidin was added to the liposomal samples, to a final indolicidin concentration of 0.5 µg/ml. The spectral values obtained for liposomes without added indolicidin were subtracted from the spectra obtained after indolicidin had been added, in order to correct for scatter. The fluorescence profile of free indolicidin in the buffer was also obtained. The excitation wavelength was set at 285 nm; emission profiles were scanned from 325 nm to 450 nm.

The results (see FIG. 6) indicate that indolicidin has a greater affinity for POPC (unsaturated) bilayers (E) than for DPPC (saturated) bilayers (C) (there is a greater difference between the relative fluorescence of free (A) and POPC-associated indolicidin than there is between the relative fluorescence of free and DPPC-associated indolicidin). Addition of cholesterol (membrane-rigidifying) to both POPC (D) and DPPC (B) decreased the affinity of indolicidin for these systems. The increase in fluorescence and blue-shift in the emission profiles indicate that indolicidin is binding deeper into POPC bilayers than is the case for any of the other systems examined.

Example 11
Order Parameters

Order parameter studies were conducted to examine the affect of indolicidin on the ordering of lipid bilayers. Indolicidin-containing DPPC, DSPC, DSPC/Chol (3:2), DHPC (dihexadecyl phosphatidylcholine), POPC, POPC/Chol/DOTAP (dioleoyl trimethlammoniopropane) (5:4:1), POPC/DOTAP and DSPC/Chol/DDAB (dimethyl dioctadecyl ammonium bromide) liposomes were prepared containing various mole percentages of indolicidin and one mole percent of the spin label 1-palmitoyl-2(12 doxyl stearoyl)-phosphatidylcholine. A stock solution of indolicidin (20 mg/ml) was prepared in HEPES buffer. The indolicidin and liposomes were combined at various mole ratios of lipid to indolicidin. DPPC (99 mg), DSPC (99 mg), DSPC/Chol (74 mg/24 mg), POPC, DOTAP (90 mg/10 mg), POPC (99 mg), POPC/DOTAP/Chol (62 mg/11 mg/25 mg) and DHPC (99 mg) were combined with 1 mg of the spin label in organic solvent so as to form solutions. The resulting solutions were dried in round-bottom flasks, and the dried lipids were rehydrated with 2.5 ml HEPES buffer so as to form liposomes (MLVs). The resultant liposome samples were transferred to cryo tubes for five freeze-thaw cycles (see Cullis et al., U.S. Pat. No. 4,975,282). The liposomes were combined with aliquots of the indolicidin stock solution to give liposomes with various mole percentages of indolicidin. The resulting liposomal indolicidin formulations were then heated above their phase transition temperatures. ESR spectra were taken at 23 degrees Celsius (room temperature). The data was used to determine the order parameters of the various liposomal indolicidin systems (see FIG. 7).

Example 12
Incorporation of Positively Charged Lipids in the Inner Monolayers of Liposomal Bilayers HEPES buffer (500 mM HEPES, pH 7.4) and a 500 mM citrate buffer were prepared; these buffers are used to prepare 290 mOsM HEPES (pH 7.4) and 290 mOsM citrate (pH 5.3) buffers.

Six lipid systems were prepared with the following lipids: I:POPC -90 mole %/stearyl amine (SA) - 10 mole % (pH 5.3):96.23 mg POPC and 3.79 mg SA; II:POPC - 90 mole %/SA - 10 mole % (pH 7.3); III:DSPC - 50 mole %/Chol - 40 mole %/SA - 10 mole % (pH 5.3):68.55 mg DSPC, 26.84 mg Chol, 4.68 mg SA; IV:DSPC - 50 mole %/Chol - 40 mole %/SA - 10 mole % (pH 7.3); V:DSPC - 60 mole %/Cholesterol - 40 mole % (pH 7.3); and VI:POPC (pH 7.3). Solutions containing these lipids are dried, and the dried lipids are resuspended, as indicated, in one of the 290 mOsM buffers so as to form multilamellar liposomes. These liposomes are then extruded through filters (see Cullis et al., U.S. Pat. No. 5,008,050 and Loughrey et al., U.S. Pat. No. 5,059,421, the contents of which are incorporated herein by reference) as follows: POPC: five times at room temperature, filter pore size=200 nm; DSPC/Chol: three times through 800 nm filters (65 degrees Celsius) and then five times through 200 nm filters (65 degrees Celsius).

Equal volumes (250 µl) of preparations of the pH 5.3 liposomes (liposomes formed by hydrating dried lipids in the pH 5.3 citrate buffer) and a pH 11.92 HEPES buffer were combined such that the final pH was about 7.3. These liposomes, comprising interior aqueous compartments which are acidic relative to the external aqueous environment, have a pH gradient across their bilayers. Preparations of liposomes formed in the pH 7.3 buffer were mixed with an equal volume (250 microliters) of the same pH 7.3 buffer and did not have transmembrane pH gradients.

Charged lipids can generally accumulate in one of the monolayers of a lipid bilayer in response to a pH gradient placed across the bilayer. The charged lipid can therefore be unevenly distributed between the inner and outer monolayers, i.e., it can have an asymmetric distribution in the bilayer (see Hope et al., U.S. Pat. Nos. 5,204,112 and 5,252,263, the contents of which are incorporated herein by reference). Lipids such as stearyl amine (SA) can generally accumulate in the inner monolayer of a lipid bilayer in response to a pH gradient placed across the bilayer, where the interior aqueous compartment is acidic relative to the external environment and has a pH less than the pKa of the lipid in the bilayer.

The pH 5.3 and the pH 7.3 liposome samples were vortexed and then incubated at room temperature (POPC-containing liposomes: 10 minutes; DSPC/Chol-containing liposomes: 1 hour). A small aliquot of each sample was removed and set aside for use in a standard phosphate assay (see Chen et al., Anal. Chem. 28:1956 (1956)) to measure lipid concentration. Next, 200 µl of a 1% polyaspartic acid solution was added to each tube, which were then allowed to stand for 10 minutes before the absorbance at 550 nm was recorded.

The results are given in Table 4 (see below). A decrease in absorbance relative to control values indicates that the charged lipid (stearyl amine) accumulates in the inner monolayer of the lipid bilayer. The results show that for POPC liposomes, stearyl amine accumulates in the inner monolayer in response to a pH gradient across the bilayer in which the interior of the liposome is acidic relative to the exterior. Stearyl amine translocation across DSPC/Chol bilayers from the outer monolayer to the inner monolayer requires more time, because of the rigidity of DSPC/Chol bilayers.

TABLE 4

ABSORBANCE OF LIPOSOMAL STEARYL AMINE FORMULATIONS IN RESPONSE TO TRANSMEMBRANE pH GRADIENTS

| Sample | $pH_{in}/pH_{out}$ | Absorbance at 550 nm |
|---|---|---|
| DSPC/Chol | 7.3/7.3 | 0.669 |
| DSPC/Chol/SA | 7.3/7.3 | 0.330 |
| DSPC/Chol/SA | 5.3/7.3 | 0.530 |
| POPC | 7.3/7.3 | 0.109 |
| POPC/SA | 7.3/7.3 | 0.645 |
| POPC/SA | 5.3/7.3 | 0.104 |

Example 13
Entrapment of Indolicidin in Positively Charged Liposomes

DSPC/Chol/DDAB liposomes (50 mole percent DSPC, 40 mole percent cholesterol, 10 mole percent DDAB) are prepared by dissolving 3.59 mg DSPC, 1.54 mg cholesterol and 0.631 mg DDAB in organic solvent in a 100-ml round-bottom flask. HEPES buffer (10 mM HEPES, 150 mM NaCl) is added to the flask and the sample is rotoevaporated to remove the organic solvent. An additional 5 ml of HEPES buffer is added to the flask, which is then heated to 65 deg. C. A further 4 ml of HEPES buffer is added, and the sample is centrifuged at 20,000 rpm for 20 minutes. The supernatant is decanted and saved; the pellet is rewashed four additional times. The final pellet is resuspended in HEPES buffer to a final volume of 1 ml. Lipid concentrations are determined by standard phosphate assay. Indolicidin concentrations are determined by absorbance spectroscopy at 280 nm.

Example 14
Hemolytic Activity of Indolicidin/Phosphatidylcholine-Containing Liposomes Indolicidin-containing POPC and DPPC liposomes were prepared in accordance with the procedures described above, but without the freeze-thaw cycles, or in the case of interdigitation-fusion (IF) vesicles, with the procedure disclosed in (Janoff et al., U.S. Ser. Nos. 07/961,277 and 08/066,539, filed Oct. 14, 1992 and May 24, 1993, respectively, the contents of which are incorporated herein by reference). Red blood cell (RBC) samples were combined with these liposomes, and the degree of hemolysis induced was measured.

The hemolysis assay used measures the level of hemoglobin in the supernatant of RBC samples, the amount of hemoglobin released to the supernatant being indicative of the damage to red blood cell membranes induced by liposomal defensins. The hemolysis assay employed phosphate buffered saline (PBS), human red blood cells, polystyrene tubes and disposable cuvettes designed for use in UV spectrophotometers. Approximately 3 ml of packed RBCs was placed in a 15 ml tube, to which 10 ml of PBS was added. The RBCs were suspended, and the suspension was centrifuged for 10 min. at 4,000 rpm. The supernatant above the pellet was discarded, and more PBS was added. This washing process was repeated until the supernatant was about clear. Two ml of the final RBC pellet was suspended in 48 ml of PBS. The resultant RBC suspension was divided amongst a set of test tubes (0.5 ml RBC suspension per tube), to which were added additional buffer and POPC/indolicidin or DPPC/indolicidin liposomes. The tubes were capped, vortexed and then incubated for 20 hours on an agitator in a 37 deg. C. incubator. After this incubation, the tubes were centrifuged at low speed (<3000 rpm) for 10 minutes. An aliquot (0.2 ml) of the supernatant from each tube was placed in a cuvette to which was added 1.0 ml of water. Hemoglobin levels in the supernatants were determined by measuring absorbance at 550 nm, and are given as percent hemolysis relative to controls. The zero percent hemolysis control comprised RBCs and HEPES buffer (the same buffer composition in which the indolicidin-containing liposomes were suspended); the one hundred percent hemolysis control comprised RBCs and distilled water.

FIG. 8 presents the percent hemolysis induced by free indolicidin (open squares), as well as by POPC/indolicidin liposomes (open triangles), DPPC/indolicidin liposomes (open circles) and DPPC/indolicidin interdigitation-fusion (IF) liposomes (filled circles). The data shows that entrapment in liposomes lessens indolicidin's hemolytic activity, i.e., there is a reduction in the percent of hemolysis, in comparison to the free form of the defensin.

Example 15
Hemolytic Activity of POPC/Indolicidin Liposomes With Varying Indolicidin Levels POPC/indolicidin liposomes, containing various indolicidin concentrations (mole percentages), were prepared by drying a POPC/organic solvent solution, and rehydrating the solution with an indolicidin-containing buffer so as to form multilamellar liposomes. Liposome samples were then transferred to cryo tubes and were frozen and thawed five times (see Cullis et al., U.S. Pat. No. 4,975,282, the contents of which are incorporated herein by reference) to produce multilamellar vesicles having substantially equal interlamellar solute distribution.

Initial and final lipid concentrations were determined by means of a standard phosphate assay (see Chen et al., Anal. Chem. 28:1956 (1956)). Initial and final indolicidin concentrations were determined by measuring absorbance at 280 nm. FIG. 9 presents the percentage RBC hemolysis induced by free indolicidin (filled squares), as well as the various indolicidin/POPC liposomal formulations tested (3.8 mole % indolicidin: filled triangles; 2.5 mole %: asterisks; 1.8 mole percent: filled circles; 1.0 mole percent: filled squares; and 0.4 mole percent: filled triangles).

Example 16
Hemolytic Activity of IndolicidinlDPPC Liposomes (8.27 Mole Percent Indolicidin)

Ethanol (361 µl) was added to five hundred µl of DPPC small unilamellar vesicles (SUVs), at a lipid concentration of 60 mg/ml so as to form a gel. An additional 1.2 ml of the DPPC SWV preparation, along with indolicidin, was then added, with vortexing. The mixture was heated and cooled, and then washed five times. Lipid concentrations in the initial and final samples were determined by a standard phosphate assay (see above). Indolicidin concentrations in the initial and final samples were determined by absorbance at 280 nm.

Hemolysis assays were conducted as described above (see Example 14). The results (see Table 5, below) indicate that increasing the indolicidin (8.27 mole % in DPPC-containing liposomes) levels (mg/ml) in the RBC samples resulted in an increased level of hemolysis.

TABLE 5

| Indolicidin Concentration in RBC Sample (mg/ml) | Average % Hemolysis |
|---|---|
| 2.73 | 163.44 |
| 1.365 | 144.34 |
| 0.6825 | 151.36 |
| 0.3413 | 149.115 |
| 0.1706 | 136.23 |
| 0.0853 | 58.3585 |
| 0.0427 | 10.9092 |
| 0.0213 | 6.71085 |
| 0.0107 | 2.68485 |
| 0.0053 | 1.13195 |

Example 17
Hemolytic Activity of DSPC/Chol/Indolicidin Liposomes

DSPC/Chol-indolicidin liposomes (final indolicidin concentration=4.8 mole percent indolicidin) were prepared by dissolving 11.85 mg DSPC, 3.87 mg cholesterol and 20 mg indolicidin in organic solvent in a round-bottom flask, and then drying the solution by rotoevaporation. The lipids were rehydrated with 4 ml HEPES buffer (10 mM HEPES, 150 mM NaCl, pH 7.4), and the resulting liposome suspension was transferred to a centrifuge tube. The flask was washed with buffer, and the buffer was then added to the centrifuge tube. These liposomes were washed with HEPES buffer five times, and the final pellet was resuspended in 3 ml of HEPES buffer. A free (unentrapped) indolicidin control was prepared by dissolving 2 mg indolicidin in 1 ml of HEPES.

Initial and final indolicidin concentrations were measured by absorbance at 280 nm. Initial and final lipid concentrations were determined by a standard phosphate assay (see Chen et al., Anal. Chem. 28:1956 (1956)). The liposomes were used in hemolysis assays, conducted in accordance with previously described procedures (see Example 14). The data (see FIG. 10 and Table 6) is presented as the percentage of hemolysis induced by free indolicidin (filled squares) as well as the percent hemolysis induced (filled circles) by the DSPC/Chol/indolicidin liposomal formulation, at various indolicidin concentrations in the RBC samples.

TABLE 6

DSPC/Cholesterol/Indolicidin Hemolysis Assay

| DSPC/CHOL/INDOLICIDIN LIPOSOMES* | | FREE INDOLICIDIN | |
|---|---|---|---|
| Indolicidin Concentration (mg/ml) | Percent Hemolysis | Indolicidin Concentration (mg/ml) | Percent Hemolysis |
| 0.77 | 110.56 | 2.00 | 140.23 |
| 0.38 | 42.57 | 1.00 | 146.40 |
| 0.19 | 10.94 | 0.50 | 152.32 |
| 0.10 | 4.77 | 0.25 | 96.13 |
| 0.05 | 2.17 | 0.13 | 56.45 |
| 0.02 | 1.50 | 0.06 | 24.19 |
| 0.01 | 0.95 | 0.03 | 8.32 |
| 0.01 | 0.40 | 0.02 | 4.16 |
| 0.003 | 1.24 | 0.008 | 1.08 |
| 0.002 | 0.32 | 0.004 | 0.89 |

*4.77 mole percent indolicidin.

Example 18
Hemolytic Activity of DSPC/Chol Liposomes (No Indolicidin)

DSPC/Chol and DSPC/Chol/DDAB liposomes were prepared by dissolving the lipids in chloroform and then adding methanol, using two volumes of methanol per volume of chloroform, so as to form a monophase (see Fountain et al., U.S. Pat. No. 4,588,578). Two 0.5 ml portions of HEPES buffer (10 mM HEPES, 150 mM NaCl, pH 7.4) were added separately, with swirling after each addition. The samples were rotoevaporated at room temperature, and then at 60 deg. C., to remove the solvent. The dried samples were rehydrated with HEPES buffer to a final volume of 4 ml so as to form multilamellar liposomes having substantially equal interlamellar solute distribution. These liposomes were combined with RBC suspensions, and hemolysis assays were conducted according to procedures described above (see Example 10) to measure the hemolytic properties of the lipids. The data (see FIG. 11 and Table 7, below) shows the percent hemolysis induced at various lipid concentrations, with no indolicidin in the preparations.

TABLE 7

LIPID HEMOLYTIC ACTIVITY

| DSPC/Chol | | DSPC/Chol/DDAB | |
|---|---|---|---|
| mM Lipid | % Hemolysis | mM Lipid | % Hemolysis |
| 9.31 | 1.46 | 5.95 | 37.14 |
| 4.66 | −0.21 | 2.98 | 15.11 |

TABLE 7-continued

| LIPID HEMOLYTIC ACTIVITY | | | |
|---|---|---|---|
| DSPC/Chol | | DSPC/Chol/DDAB | |
| mM Lipid | % Hemolysis | mM Lipid | % Hemolysis |
| 2.33 | 0.90 | 1.49 | 3.03 |
| 1.16 | −0.33 | 0.74 | 1.13 |
| 0.58 | −0.27 | 0.37 | 0.35 |
| 0.29 | −0.77 | 0.19 | 0.46 |
| 0.15 | 0.01 | 0.09 | 0.07 |
| 0.07 | −0.94 | 0.05 | 0.35 |
| 0.04 | 0.85 | 0.02 | −0.55 |
| 0.02 | −1.05 | 0.01 | −0.38 |

Example 19
Hemolytic Activity of Indolicidin/DOPE Liposomes

DOPE/indolicidin liposomes were prepared by drying an indolicidin/DOPE/organic solvent solution, in a round-bottom flask, by rotoevaporation. The dried lipids were resuspended in 2 ml of HEPES buffer (10 mM HEPES, 150 mM NaCl). A free (unentrapped) indolicidin control was prepared by dissolving 2 mg of indolicidin in 1 ml of HEPES buffer. Lipid concentrations were determined by phosphate assay (see Chen et al., Anal. Chem. 28:1956 (1956)); indolicidin concentrations were determined by measuring absorbances at 280 nm. The data (see FIG. 12 and Table 8, below) show that hemolysis generally increased with increasing indolicidin concentration, both for the liposomal and free forms of indolicidin, and that at approximately the same concentrations in the RBC samples, indolicidin entrapped in DOPE liposomes induced about the same percentage of hemolysis as did unentrapped indolicidin.

TABLE 8

| HEMOLYTIC ACTIVITY OF DOPE/INDOLICIDIN LIPOSOMES | | | |
|---|---|---|---|
| INDOLICIDIN/DOPE LIPOSOMES* | | FREE INDOLICIDIN | |
| Indolicidin Concentration (mg/ml) | Percent Hemolysis | Indolicidin Concentration (mg/ml) | Percent Hemolysis |
| 3.83 | 113.45 | 2.00 | 82.44 |
| 1.92 | 114.91 | 1.00 | 100.90 |
| 0.96 | 122.46 | 0.50 | 116.16 |
| 0.48 | 124.65 | 0.25 | 84.53 |
| 0.24 | 116.14 | 0.13 | 40.81 |
| 0.12 | 70.65 | 0.06 | 16.89 |
| 0.06 | 34.38 | 0.03 | 7.70 |
| 0.03 | 13.92 | 0.02 | 0.80 |
| 0.01 | 5.96 | 0,008 | −1.01 |
| 0.007 | 1.88 | 0.004 | −0.79 |

*39.55 mole percent indolicidin.

Example 20
In Vitro Liposomal Indolicidin Toxicity

Liposomes were prepared by dissolving 1 mg of indolicidin in methanol and mixing the resultant solution with a POPC (11.7 mg) chloroform solution (indolicidin:lipid ratio (w/w) of 0.85:1). The organic solvents were removed under vacuum using a rotary evaporator. The dried lipid/indolicidin mixture was hydrated with HEPES buffer (10 mM HEPES, 150 mM NaCl, pH 7.4). The resulting preparation was extruded ten times through double-stacked 0.1 µm Nucleopore filters using an extruder device (Lipex, Vancouver, Calif.).

The specific inhibition of in vitro proliferation of CHO/K1 cells by free indolicidin, empty liposomes (no indolicidin) or liposomal indolicidin was measured using a thymidine incorporation assay. CHO/K1 cells (20,000 cells per well) were plated onto 96 well flat-bottomed microtiter plates in RPMI-1640 medium supplemented with 10% FBS, and kept at 37° C. in a humidified atmosphere at 5% $CO_2$. The cells were exposed to various concentrations of either empty liposomes, phosphate-buffered saline (PBS), free indolicidin or liposomal-indolicidin and cultured for 4 hours at 37° C. Cells treated with various formulations of indolicidin were pulsed for another eight hours with 0.5µCi/well of [$^3$H]thymidine (specific activity 50 ci/mmol) (ICN Biomedicals, USA). Cells were harvested on 934AH filter paper with Brandel M-96 harvester (Brandel, Md., U.S.A.). Thymidine [$^3$H] incorporation was determined by liquid scintillation counting.

The results (see FIG. 13) show that at all indolicidin concentrations used, liposomal indolicidin permitted a greater degree of cell growth, i.e., was less toxic, than was free indolicidin.

Example 21
In Vivo Toxicity

Four groups of five male Balb/c mice each (20–22 g) were injected with various doses (0.75–12 mg/kg) of free indolicidin and various doses (20–120 mg/kg) of liposomal indolicidin in 0.2 ml of pyrogen-free saline via the tail vein. Mice were also injected with saline and with empty liposomes. These mice were observed for acute toxicity, and the $LD_{50}$ dose of indolicidin, that dose lethal to 50 percent of the test population, was determined.

The results (see Table 9, below) indicate that the $LD_{50}$ of free indolicidin was 3 mg/kg while that for liposomal indolicidin was 80 mg/kg.

TABLE 9

| TOXICITY OF FREE VS. LIPOSOMAL INDOLICIDIN IN MICE | |
|---|---|
| Indolicidin Dose (mg/kg) | Number of Animals Dead |
| FREE INDOLICIDIN | |
| 0.4 | 0/5 |
| 1.2 | 1/5 |
| 4.0 | 3/5 |
| 12.0 | 0/5 |
| LIPOSOMAL INDOLICIDIN | |
| 20 | 0/5 |
| 40 | 0/5 |
| 80 | 1/5 |
| 160 | 5/5 |

Example 22
Treatment of Aspergillus Fumigatus Infections in Mice

Male Balb/c mice were each injected with $2 \times 10^7$ Aspergillus fumigatus spores by injection in the tail vein. After six hours, the mice were randomly divided into five groups of 10 mice each. One group was treated with 2 mg/kg free indolicidin, the second was treated with 2 mg/kg of liposomal indolicidin; the third group was a administered 40 mg/kg of liposomal indolicidin; the fourth group was treated with empty liposomes; and the fifth group was treated with 0.2 ml of 10 mM HEPES buffer. The animals' survival was monitored over a 15-day period.

The results (see FIG. 14) mice infected with A. fumigatus spores and administered either buffer or empty liposomes exhibited about the same survival rates. Administration of free indolicidin (2 mg/kg) resulted in a slight increase in survival times. Liposomal indolicidin at the same indolicidin concentration elicited an even greater increase in survival times. Thirty percent of the mice given 40 mg/ml indolicidin were alive at the end of the treatment period.

What is claimed is:

1. A method of treating a mammal for an infection by a microbe sensitive to a defensin, the method comprising administering to the mammal a liposome comprising:

(a) a bilayer comprising a lipid which comprises palmitoyloleoyl phosphatidylcholine, dioleoyl phosphatidylcholine or distearoyl phosphatidylcholine and cholesterol;

(b) an internal compartment comprising an aqueous buffer; and, (c) a neutralized defensin selected from the group consisting of prototypical mammalian defensins, beta-defensins, indolicidin, magainins and insect defensins, wherein an amount of the liposome comprising an anti-infection effective amount of the defensin is administered.

2. The method of claim 1, wherein the mammal is an immunocompromised human.

3. The method of claim 1, wherein the microbe is a fungus.

4. The method of claim 1, wherein the mammal is an immunocompromised human and the infection is by a fungus selected from the group consisting of Aspergilli and Cryptococci.

5. The method of claim 1, wherein the anti-infection effective amount of the defensin is between about 1 and about 1000 mg of the defensin per kg of the mammal's body weight.

6. A method of treating a mammal afflicted with a cancer responsive to a defensin, the method comprising administering to the mammal a liposome comprising:

(a) a bilayer comprising a lipid which comprises palmitoyloleoyl phosphatidylcholine, dioleoyl phosphatidylcholine or distearoyl phosphatidylcholine and cholesterol;

(b) an internal compartment comprising an aqueous buffer; and, (c) a neutralized defensin selected from the group consisting of prototypical mammalian defensins, beta-defensins, indolicidin, magainins and insect defensins, wherein an amount of the liposome comprising an anticancer effective amount of the defensin is administered to the mammal.

7. The method of claim 6, wherein the cancer is a leukemia or lymphoma.

8. The method of claim 6, wherein the anticancer effective amount of the defensin is between about 1 and about 1000 mg of the defensin per kg of the mammal's body weight.

9. The method of claim 1 or 6, wherein the liposome has multiple bilayers.

10. The multilamellar liposome of claim 9 having a solute entrapped in its internal compartments, wherein the concentration of solute in each of the compartments is substantially equal.

11. The method of claim 1 or 6, wherein the defensin is indolicidin.

12. The method of claim 1 or 6, wherein the defensin is associated with the bilayer.

13. The method of claim 1 or 6, wherein the defensin is entrapped in an internal compartment of the liposome.

14. The method of claim 1 or 6, wherein the defensin comprises at most about 20 mole percent of the liposome.

15. The method of claim 1 or 6, wherein the aqueous buffer is a citrate buffer.

16. The method of claim 1 or 6, wherein the lipid further comprises an ionizable cationic lipid.

17. The liposome of claim 16, wherein the lipid further comprises about 5 mole percent of the lipid 1,2-dipalmitoyl-3-(N,N-dimethylamino)-propane.

18. The method of claim 1 or 6 wherein the lipid further comprises a headgroup-modified lipid.

19. The method of claim 1 or 6, wherein the liposome comprises an additional bioactive agent selected from the group consisting of antiparasitic, antifungal, antibacterial or antineoplastic compounds.

20. The method of claim 1 or 6, wherein the lipid comprises dioleoyl phosphatidylcholine, wherein the liposome comprises a citrate buffer and about 0.5 mole percent of the defensin indolicidin, and wherein the liposome is a multilamellar liposome having substantially equal interlamellar solute distribution.

21. The method of claim 1 or 6, wherein the lipid comprises distearoyl phosphatidylcholine and cholesterol, wherein the liposome comprises a citrate buffer and about 0.5 mole percent of the defensin indolicidin, and wherein the liposome is a multilamellar liposome having substantially equal interlamellar solute distribution.

22. The method of claim 1 or 6, wherein the liposome is dehydrated and subsequently rehydrated prior to administration.

* * * * *